(12) United States Patent
Bleiholder

(10) Patent No.: US 10,605,773 B2
(45) Date of Patent: Mar. 31, 2020

(54) DETERMINING MOLECULAR AND MOLECULAR ASSEMBLY STRUCTURES FROM A MOMENTUM TRANSFER CROSS SECTION DISTRIBUTION

(71) Applicant: The Florida State University Research Foundation, Inc., Tallahassee, FL (US)

(72) Inventor: Christian Bleiholder, Tallahassee, FL (US)

(73) Assignee: The Florida State University Research Foundation, Inc., Tallahassee, FL (US)

(*) Notice: Subject to any disclaimer, the term of this patent is extended or adjusted under 35 U.S.C. 154(b) by 0 days.

(21) Appl. No.: 16/332,117

(22) PCT Filed: Jun. 6, 2017

(86) PCT No.: PCT/US2017/036106
§ 371 (c)(1),
(2) Date: Mar. 11, 2019

(87) PCT Pub. No.: WO2018/057070
PCT Pub. Date: Mar. 29, 2018

(65) Prior Publication Data
US 2019/0302054 A1    Oct. 3, 2019

Related U.S. Application Data

(60) Provisional application No. 62/397,665, filed on Sep. 21, 2016.

(51) Int. Cl.
*G01N 27/00*   (2006.01)
*G01N 27/62*   (2006.01)
(Continued)

(52) U.S. Cl.
CPC ........... *G01N 27/622* (2013.01); *G16C 20/50* (2019.02); *H01J 49/0036* (2013.01); *H01J 49/40* (2013.01)

(58) Field of Classification Search
CPC ... G01N 27/622; G16C 20/50; H01J 49/0036; H01J 49/40
(Continued)

(56) References Cited

U.S. PATENT DOCUMENTS

2004/0219545 A1   11/2004   Rando et al.
2005/0065733 A1   3/2005    Caron et al.
(Continued)

FOREIGN PATENT DOCUMENTS

WO   2015/123632 A1   8/2015

OTHER PUBLICATIONS

Duhrkop, et al ("Searching molecular structure databases with tandem mass spectra using CSI:FingerID" PNAS vol. 112, No. 41, pp. 12580-12585, 2015) (Year: 2015).*
(Continued)

*Primary Examiner* — Michael Maskell
(74) *Attorney, Agent, or Firm* — Eversheds Sutherland (US) LLP

(57) ABSTRACT

Provided are systems and methods for de novo determinations of molecular structures or assemblies, including biologically relevant protein structures or assemblies, from IMS-MS data alone. The systems and methods perform a comprehensive conformational analysis of a molecule or molecular assembly, predict IMS-MS spectra for the molecule or molecular assembly, and report structures that best explain experimental spectra for the molecule or molecular assembly.

22 Claims, 18 Drawing Sheets

(51) Int. Cl.
*G16C 20/50* (2019.01)
*H01J 49/00* (2006.01)
*H01J 49/40* (2006.01)

(58) Field of Classification Search
USPC .............. 250/281, 282, 287; 702/22–28
See application file for complete search history.

(56) References Cited

U.S. PATENT DOCUMENTS

| | | |
|---|---|---|
| 2006/0228730 A1 | 10/2006 | Rando et al. |
| 2013/0303383 A1 | 11/2013 | Sander et al. |
| 2014/0138531 A1 | 5/2014 | Wright |
| 2019/0265195 A1* | 8/2019 | Park ................. G01N 27/622 |

OTHER PUBLICATIONS

PCT International Search Report and Written Opinion for PCT Application No. PCT/US2017/036106 dated Aug. 25, 2017 (20 pages).

Damjanovic et al., "Backbone Relaxation Coupled to the Ionization of Internal Groups in Proteins: A Self-Guided Langevin Dynamics Study," Biophysical Journal, 2008, 95:4091-4101.

DeBartolo et al., "Protein Structure Prediction Enhanced with Evolutionary Diversity: SPEED," Protein Science, 2010, 19:520-534.

Duhrkop et al., "Searching Molecular Structure Databases with Tandem Mass Spectra Using CSI:FingerID," PNAS, 2015, 112(41):12580-12585.

Kind et al., "Advances in Structure Elucidation of Small Molecules using Mass Spectrometry," Bional Rev, 2010, 2:23-60.

Xiao et al., "Metabolite Identification and Quantitation in LC-MS/MS-baed Metabolomics," Trends Anlyt. Chem., 2012, 32:1-14.

\* cited by examiner

DETERMINING MOLECULAR AND MOLECULAR ASSEMBLY STRUCTURES FROM A MOMENTUM TRANSFER CROSS SECTION DISTRIBUTION

CROSS-REFERENCE TO RELATED APPLICATIONS

This application claims priority benefit of U.S. Provisional Application No. 62/397,665, filed Sep. 21, 2016, which is incorporated by reference herein in its entirety.

FIELD OF THE INVENTION

This disclosure relates generally to determining molecular and molecular assembly structures from ion mobility-mass spectrometry (IM-MS) data.

BACKGROUND OF THE INVENTION

Protein structure and protein assemblies play a crucial role in disease etiology because protein function is intimately linked to its structure. For example, the common neurodegenerative disorders Parkinson's and Alzheimer's disease result from the misfolding and aggregation of specific proteins. The proteins associated with these diseases resemble prion-like pathogens because they form self-propagating protein assemblies through a dynamic process: individual proteins combine to form small protein assemblies and small protein assemblies combine to form large protein assemblies. This dynamic process involves unfolding and/or rearranging protein and/or protein assembly structures. More generally, many of the fastest growing major diseases in the United States, such as Alzheimer's disease, Parkinson's disease, diabetes mellitus type 2, atherosclerosis, and cancer, involve transiently populated conformations of proteins and their assemblies.

Nuclear magnetic resonance (NMR) and x-ray spectroscopy provide ensemble-averaged structures of proteins and have been invaluable for pharmaceutical research. However, these techniques are not well-suited for elucidating detailed structures of dynamic proteins and their complexes. The existing techniques do not capture co-existing, transiently populated protein conformations because they only measure ensemble-averaged structures of proteins. The inability to elucidate co-existing, transient protein conformations has hampered efforts to develop pharmacological strategies for treating or preventing many diseases because a clear molecular target for drug development cannot be discerned.

Ion mobility spectrometry-mass spectrometry (IMS-MS) has been used for structural characterization of generally small organic and inorganic molecules. Recent advancements in the field have led to equipment modifications that allow IMS-MS to be used for research involving large, macromolecular organic and biological compounds. IMS-MS is capable of revealing transient protein structures, and is well suited to study co-existing, transient conformations of proteins and their complexes because it physically separates analytes that differ in mass and shape within milliseconds. IMS-MS can be accomplished using minute amounts of sample within seconds due to the high sensitivity and speed of MS analysis. However, IMS-MS only measures an orientation-averaged cross section of a protein or a protein assembly. Structural details are not revealed by IMS-MS data, and extracting detailed molecular structures from IMS-MS data alone is challenging.

There are no known methods for extracting de novo detailed molecular structures from measured cross sections alone. Current state of the art methods couple structures from traditional techniques (e.g. NMR) with IMS-MS data analysis. However, this approach cannot exploit the full potential of IMS-MS, which is to elucidate structures for exactly those systems where traditional methods fail. Other methods report structures when computed cross sections for theoretical (average) model structures match experimental data or use experimental cross sections as a "filter" to select a specific structure from a pool of computed model structures; however, these methods suffer from many shortcomings. First, different protein structures can have identical cross sections. Second, the experimental cross section may be the average of the cross sections of distinct structures that interconvert in the experiment. Third, protein dynamics in the IMS-MS experiment depend on the charge state. Therefore, there is a need for improved systems and methods that can extract detailed structural information of molecules from IMS-MS data.

SUMMARY OF THE INVENTION

Methods for determining a molecular structure of a molecule are provided. In embodiments, the methods comprise: determining, based on a Lewis structure of a molecule, a plurality of candidate molecule structures of the molecule; determining a predicted time-resolved ion mobility mass spectrometry (TRIM-MS) spectra for each of the candidate molecule structures; determining, based at least in part on a measure of similarity between a measured TRIM-MS spectrum of the molecule and each of the predicted TRIM-MS spectra, a subset of candidate molecule structures; determining a candidate score for each candidate molecule structure in the subset; and assigning, based on the candidate scores, a molecular structure of the molecule.

Methods for determining a molecular structure of a molecular assembly are provided. In embodiments, the methods comprise: determining, for a molecule, a plurality of candidate molecular assemblies; determining a predicted time-resolved ion mobility mass spectrometry (TRIM-MS) spectra for each of the candidate molecular assemblies; determining, based at least in part on a measure of similarity between a measured TRIM-MS spectrum of a molecular assembly of the molecule and each of the predicted TRIM-MS spectra, a subset of candidate molecular assemblies; determining a candidate score for each candidate molecular assembly in the subset; and assigning, based on the candidate scores, a molecular assembly of the molecule.

Devices for determining a molecular structure of a molecule are provided. In embodiments, the devices comprise memory and processing circuitry configured to: determine, based on a Lewis structure of a molecule, a plurality of candidate molecule structures of the molecule; determine a predicted time-resolved ion mobility mass spectrometry (TRIM-MS) spectra for each of the candidate molecule structures; determine, based at least in part on a measure of similarity between a measured TRIM-MS spectrum of the molecule and each of the predicted TRIM-MS spectra, a subset of candidate molecule structures; determine a candidate score for each candidate molecule structure in the subset; and assign, based on the candidate scores, a molecular structure of the molecule.

Devices for determining a molecular structure of a molecular assembly are provided. In embodiments, the devices comprise memory and processing circuitry configured to: determine, for a molecule, a plurality of candidate molecular assemblies; determine a predicted time-resolved ion mobility mass spectrometry (TRIM-MS) spectra for each of the candidate molecular assemblies; determine, based at least in part on a measure of similarity between a measured TRIM-MS spectrum of a molecular assembly of the molecule and each of the predicted TRIM-MS spectra, a subset of candidate molecular assemblies; determine a candidate score for each candidate molecular assembly in the subset; and assign, based on the candidate scores, a molecular assembly of the molecule.

A non-transitory computer-readable medium storing computer-executable instructions for determining a molecular structure of a molecule is provided. In embodiments, the non-transitory computer-readable medium stores computer-executable instructions which, when executed by one or more processors, result in performing operations comprising: determining, based on a Lewis structure of a molecule, a plurality of candidate molecule structures of the molecule; determining a predicted time-resolved ion mobility mass spectrometry (TRIM-MS) spectra for each of the candidate molecule structures; determining, based at least in part on a measure of similarity between a measured TRIM-MS spectrum of the molecule and each of the predicted TRIM-MS spectra, a subset of candidate molecule structures; determining a candidate score for each candidate molecule structure in the subset; and assigning, based on the candidate scores, a molecular structure of the molecule.

A non-transitory computer-readable medium storing computer-executable instructions for determining a molecular structure of a molecular assembly is provided. In embodiments, the non-transitory computer-readable medium stores computer-executable instructions which, when executed by one or more processors, result in performing operations comprising: determining, for a molecule, a plurality of candidate molecular assemblies; determining a predicted time-resolved ion mobility mass spectrometry (TRIM-MS) spectra for each of the candidate molecular assemblies; determining, based at least in part on a measure of similarity between a measured TRIM-MS spectrum of a molecular assembly of the molecule and each of the predicted TRIM-MS spectra, a subset of candidate molecular assemblies; determining a candidate score for each candidate molecular assembly in the subset; and assigning, based on the candidate scores, a molecular assembly of the molecule.

BRIEF DESCRIPTION OF THE DRAWINGS

FIG. 3A shows the development of time-resolved IMS-MS methods that include equations which relate the measured arrival time to the cross section of an ion in electrodynamics fields. FIG. 3B shows that, on the basis of the equations in FIG. 3A, measuring absolute cross sections directly from the experimental data can be accomplished without calibration and within the error of traditional drift tube systems. FIG. 3C shows that time resolved IMS-MS achieves resolving powers >250, while other IMS-MS systems achieve resolutions between 40 and 100. FIG. 3D shows the characterized performance of time-resolved measurements in the IMS device of FIG. 2.

FIG. 6A shows time-resolved IMS-MS cross section distributions for ubiquitin 6+ and 7+ charge states. The experimental data obtained by "soft" and collision-activated instrument settings show native-like features (~NMR) that are stable on the timescale of seconds and gasphase structures emerge (see overlap after 12.387 s). FIG. 6B compares experimental (6+, "soft" settings, 0.002 s and 12.387 s, see FIG. 6A) with predicted time-resolved IMS-MS spectra. Broad peaks indicate the presence of several, unresolved protein conformations.

DETAILED DESCRIPTION

General Description

Figure 1:
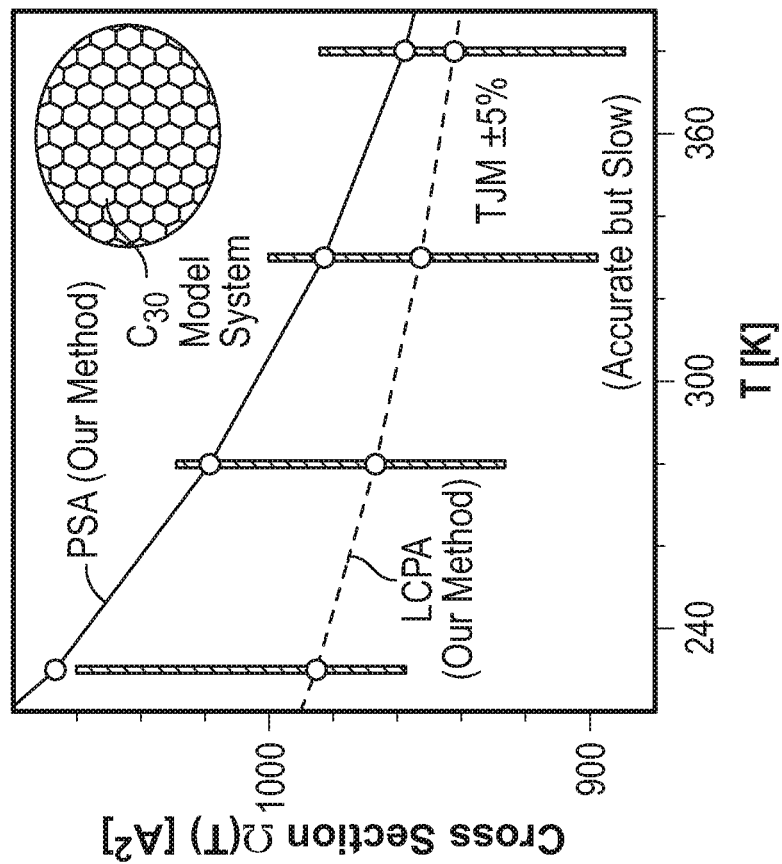
FIG. 1 shows cross section calculations for IMS-MS data using local collision probability approximation (LCPA), projection approximation (PSA), and trajectory method (TJM) algorithms. The PSA and LCPA algorithms are as accurate as the TJM but much faster. Projection approximations are inaccurate (~30% error).
Figure 1:
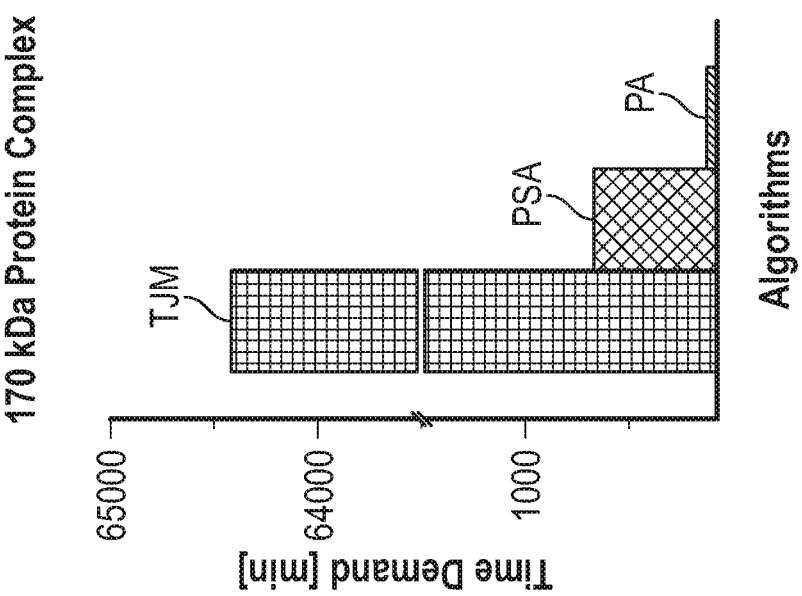

The present disclosure allows for de novo determinations of molecular structures or assemblies, including biologically relevant protein structures or assemblies, from IMS-MS data alone. At a high level, the systems and methods: perform a comprehensive conformational analysis of a molecule based on its Lewis structure; predict IMS-MS spectra by accounting for charge-state specific molecular dynamics in the gas phase; and select and report the structures that best explain the experimental spectra. More specifically, the systems and methods: use the Lewis structure of a molecule to compute a number of potential conformational structures (e.g. 3-D structures) for the molecule; compute expected IMS-MS data for the potential conformational structures; compare the calculated IMS-MS data for the potential conformational structures with measured (i.e. real) IMS-MS data for the molecule; and determine, based at least in part on the compared calculated IMS-MS data with measured IMS-MS data, a molecular structure of the molecule.

The present disclosure allows for elucidating three dimensional structures of molecules and molecule aggregates (e.g. secondary, tertiary, quaternary, and aggregated structures of molecules), including transiently populated conformations of molecules like proteins, in a high-throughput, automated matter. One advantage of the present disclosure is that a priori knowledge of a molecule's three-dimensional structure is not needed to determine the structure of the molecule. The systems and methods can take in, as inputs, (1) a Lewis structure of a molecule (e.g. a protein primary structure or amino acid sequence); and (2) an experimental IMS-MS spectrum of the molecule (e.g. a spectrum measured in a laboratory experiment). From these two inputs, the systems and methods can report the most likely structural conformation(s) of the molecule.

In some aspects, the systems and methods of the present disclosure can identify co-existing, transient, interconverting conformations of molecules and their complexes, which prior systems and methods have been unable to do. The deduced structures can be used for a variety of purposes, such as improving drug development and discovery for diseases. For example, the present disclosure allows for rapidly revealing molecular mechanisms of complex biological processes and allows for improved drug screening by virtue of having detailed knowledge of relevant molecular structure features (e.g. binding sites, similarity to other known molecules, how molecules are attached to each other, etc.).

In an exemplary embodiment, the systems and methods of the present disclosure determine molecular structures by, in part, using computational LCPA (Local Collision Probability Approximation) and PSA (Projection Approximation) algorithms to calculate predicted cross sections for charge state specific model structures of a molecule, and comparing time-resolved, trapped, charge-state specific experimental IMS-MS spectra with predicted IMS-MS spectra. The systems and methods of the present disclosure can predict time-resolved IMS-MS spectra for each distinct charge state of a molecule (e.g. a protein) for comparison to experimental IMS-MS spectra. The PSA and LCPA methods make it possible to accurately calculate thousands of cross sections for prediction of entire IMS-MS spectra for molecular structures. This holds especially when experiments are carried out with nitrogen buffer gas which is used by all commercially available IMS-MS systems. In embodiments, possible molecular conformations are screened by fast empirical methods, and only short molecular dynamics simulations are used for conformation refinement.

Throughout parts of the disclosure, the invention is described in reference to an exemplary embodiment: elucidating protein and protein assembly structures. However, this is not intended to be limiting and the invention generally applies to any organic or inorganic molecule. Thus, any exemplary disclosures herein regarding determining protein structures/assemblies can be applied more generally to any molecules (e.g. sugars, nucleic acids, etc.), and determining molecular structures/assemblies of any type of molecule are within the scope of the present invention.

Figure 14:
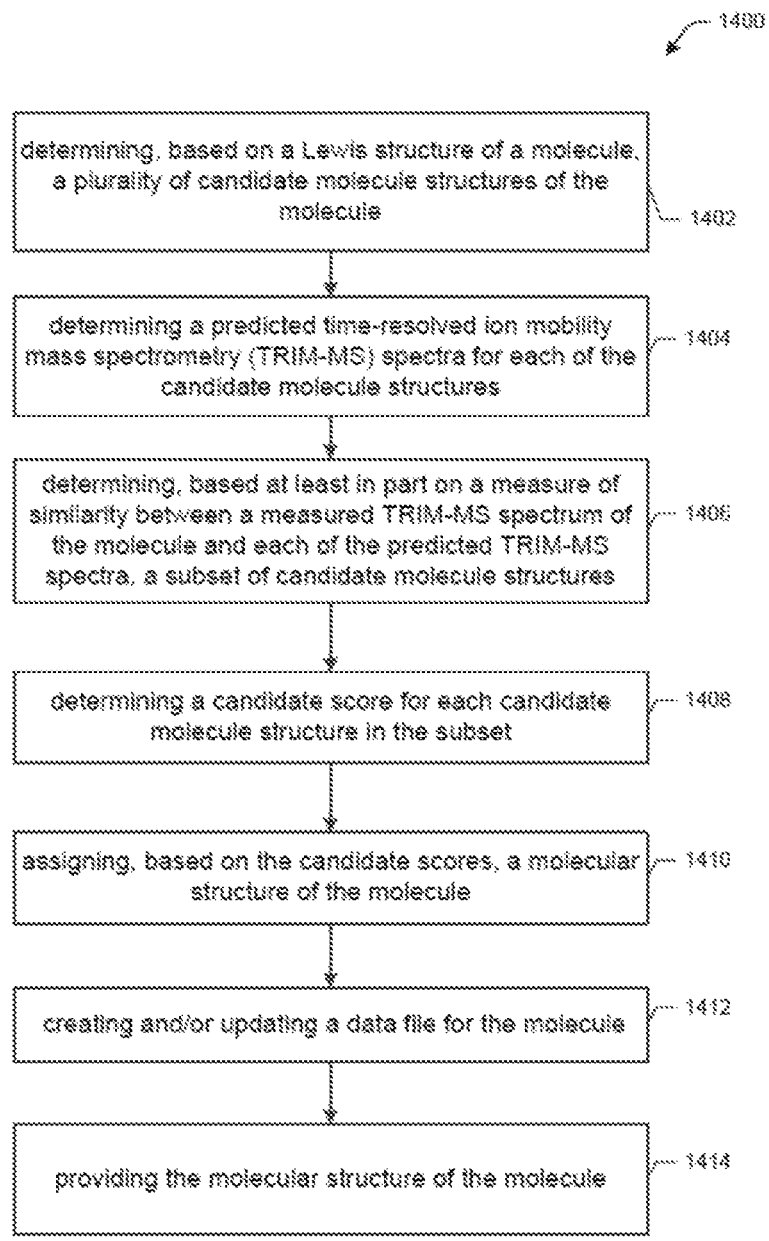
FIG. 14 shows a method for determining a molecular structure of a molecule in accordance with embodiments of the present disclosure.

Provided herein are methods for determining a molecular structure of a molecule 1400, as illustrated in FIG. 14. The methods can include one or more of the following: determining, based on a Lewis structure of a molecule, a plurality of candidate molecule structures of the molecule 1402; determining a predicted time-resolved ion mobility mass spectrometry (TRIM-MS) spectra for each of the candidate molecule structures 1404; determining, based at least in part on a measure of similarity between a measured TRIM-MS spectrum of the molecule and each of the predicted TRIM-MS spectra, a subset of candidate molecule structures 1406; determining a candidate score for each candidate molecule structure in the subset 1408; assigning, based on the candidate scores, a molecular structure of the molecule 1410; creating and/or updating a data file for the molecule 1412; and/or providing the molecular structure of the molecule 1414.

In embodiments, the methods of the present disclosure include determining, based on a Lewis structure of a molecule, a plurality of candidate molecule structures of a molecule. In embodiments, the determining the plurality of candidate molecule structures can include: determining, based on the Lewis structure of the molecule, a plurality of initial candidate structures using an unbiased conformational search; determining an ionized candidate structure for each of the initial candidate structures, wherein each of the ionized candidate structures have a same charge state; and determining, by relaxing each of the ionized candidate structures in a molecular dynamics simulation, the candidate molecule structure for each of the ionized candidate structures.

In embodiments, the methods of the present disclosure include determining a predicted time-resolved ion mobility mass spectrometry (TRIM-MS) spectra for each of the candidate molecule structures. In embodiments, the determining the predicted TRIM-MS spectra for each of the candidate molecule structures includes determining collision cross sections for each of the candidate molecule structures; and determining, based on the collision cross sections, the predicted TRIM-MS spectra for each of the candidate molecule structures. In embodiments, the collision cross sections for each of the candidate molecule structures is determined by projection superposition approximation (PSA) or local collision probability approximation (LCPA). In embodiments, the subset of candidate molecule structures is each candidate molecule structure whose corresponding predicted TRIM-MS spectra, when shifted by a $\delta\Omega$ value, overlaps with the measured TRIM-MS spectrum.

In embodiments, the methods of the present disclosure include determining, based at least in part on a measure of similarity between a measured TRIM-MS spectrum of the molecule and each of the predicted TRIM-MS spectra, a subset of candidate molecule structures.

In embodiments, the methods of the present disclosure include determining a candidate score for each candidate molecule structure in the subset. In embodiments, determining the candidate score for each candidate molecule structure in the subset includes determining, for each candidate molecule structure in the subset, an atom-atom distance probability distribution for each atom-atom pair; and determining, for each candidate molecule structure in the subset, the candidate score based on a joint probability based on the atom-atom distance probability distribution for each atom-atom pair.

In embodiments, the methods of the present disclosure include assigning, based on the candidate scores, a molecular structure of the molecule. In embodiments, assigning the molecular structure of the molecule includes determining the molecular structure of the molecule is the candidate molecule structure corresponding to a highest ranking candidate score.

In embodiments, the methods of the present disclosure include creating and/or updating a data file for the molecule. In embodiments, the date file includes an identifier of the molecule; and the molecular structure of the molecule.

In embodiments, the methods of the present disclosure include providing the molecular structure of the molecule. In embodiments, providing the molecular structure of the molecule includes displaying an image of the molecular structure of the molecule, displaying coordinates of the molecular structure of the molecule, sending the image of the molecular structure of the molecule, sending coordinates of the molecular structure of the molecule, or a combination thereof.

Figure 15:
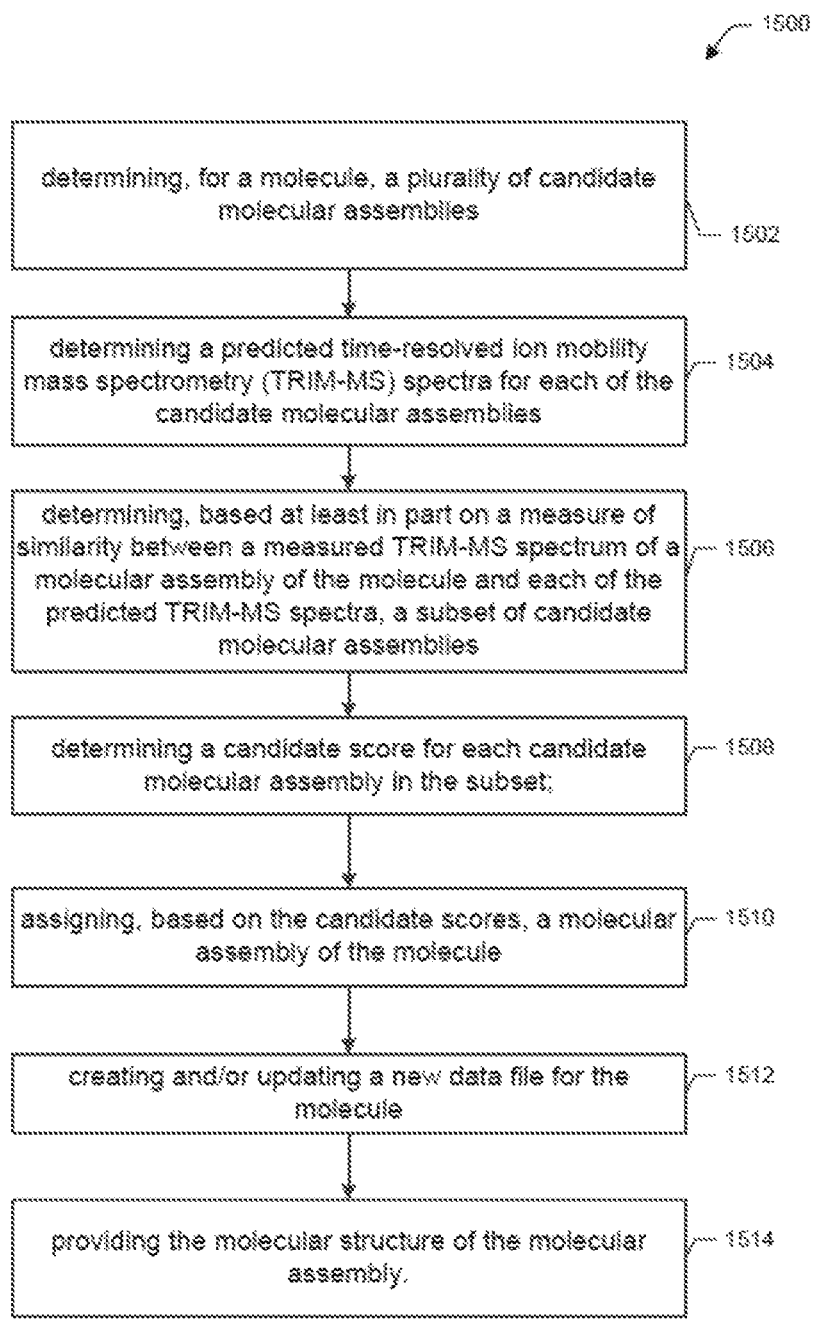
FIG. 15 shows a method for determining a molecular structure of a molecular assembly in accordance with embodiments of the present disclosure.

Provided herein are methods for determining a molecular structure of a molecular assembly 1500, as illustrated in FIG. 15. The methods can include one or more of the following: determining, for a molecule, a plurality of candidate molecular assemblies 1502; determining a predicted time-resolved ion mobility mass spectrometry (TRIM-MS) spectra for each of the candidate molecular assemblies 1504; determining, based at least in part on a measure of similarity between a measured TRIM-MS spectrum of a molecular assembly of the molecule and each of the predicted TRIM-MS spectra, a subset of candidate molecular assemblies 1506; determining a candidate score for each candidate molecular assembly in the subset 1508; assigning, based on the candidate scores, a molecular assembly of the molecule 1510; creating and/or updating a new data file for the molecule 1512; and/or providing the molecular structure of the molecular assembly 1514.

In embodiments, the methods of the present disclosure include determining, for a molecule, a plurality of candidate molecular assemblies. In embodiments, determining the plurality of candidate molecular assemblies includes docking, by a macromolecular docking algorithm, one or more of the molecule, one or more assemblies of the molecule, or a combination thereof, with one another to form the plurality of candidate molecular assemblies. In embodiments, the molecular macromolecular docking algorithm is ZDOCK or HADDOCK.

In embodiments, the methods of the present disclosure include determining a predicted time-resolved ion mobility mass spectrometry (TRIM-MS) spectra for each of the candidate molecular assemblies. In embodiments, determining the predicted TRIM-MS spectra for each of the candidate molecular assemblies includes determining collision cross sections for each of the candidate molecular assemblies; and determining, based on the collision cross sections, the predicted TRIM-MS spectra for each of the candidate molecular assemblies. In embodiments, the collision cross sections for each of the candidate molecular assemblies is determined by projection superposition approximation (PSA) or local collision probability approximation (LCPA).

In embodiments, the methods of the present disclosure include determining, based at least in part on a measure of similarity between a measured TRIM-MS spectrum of a molecular assembly of the molecule and each of the predicted TRIM-MS spectra, a subset of candidate molecular assemblies. In embodiments, the subset of candidate molecular assemblies is each candidate molecular assembly whose corresponding predicted TRIM-MS spectra, when shifted by a $\delta\Omega$ value, overlaps with the measured TRIM-MS spectrum.

In embodiments, the methods of the present disclosure include determining a candidate score for each candidate molecular assembly in the subset. In embodiments, determining the candidate score for each candidate molecular assembly in the subset includes cross-correlating the measured TRIM-MS spectrum of the molecular assembly of the molecule with each of the predicted TRIM-MS spectra. In embodiments, determining the candidate score for each candidate molecular assembly in the subset includes determining a probability ranking for each candidate molecular assembly in the subset.

In embodiments, the methods of the present disclosure include assigning, based on the candidate scores, a molecular assembly of the molecule. In embodiments, assigning the molecular structure of the molecular assembly includes determining the molecular structure of the molecular assembly is the candidate molecular assembly corresponding to a highest ranking candidate score.

In embodiments, the methods of the present disclosure include creating and/or updating a new data file for the molecule. In embodiments, the data file includes an identifier of the molecule; and the molecular structure of the molecular assembly.

In embodiments, the methods of the present disclosure include providing the molecular structure of the molecular assembly. In embodiments, providing the molecular structure of the molecular assembly includes displaying an image of the molecular structure of the molecular assembly, displaying coordinates of the molecular structure of the molecular assembly, sending the image of the molecular structure of the molecular assembly, sending coordinates of the molecular structure of the molecular assembly, or a combination thereof.

In embodiments, the methods of the present disclosure determine a molecular structure of a molecule or a molecular assembly. In embodiments, the molecule or molecular assembly is an organic molecule or organic molecular assembly. In embodiments, the molecule or molecular assembly is an inorganic molecule or inorganic molecular assembly. In embodiments, the molecule or molecular assembly is a biomolecule or biomolecular assembly. In embodiments, the molecule or molecular assembly is a protein or protein assembly. The building block (repeating unit) of a protein is amino acids. In embodiments, the molecule or molecular assembly is a nucleic acid (e.g. DNA, RNA) or nucleic acid assembly. The building block (repeating unit) of a nucleic acid is nucleotides (e.g. deoxyribonucleotides, ribonucleotides). In embodiments, the molecule or molecular assembly is a saccharide or saccharide assembly. The building block (repeating unit) of a saccharide is monosaccharide. In embodiments, the molecule or molecular assembly is a lipid or lipid assembly. The building block (repeating unit) of a lipid is fatty acids and glycerol.

Provided herein are methods for drug screening. The methods can include screening a potential therapeutic against the molecular structure of a molecule or molecular assembly determined in accordance with embodiments of the present disclosure.

Figure 16:
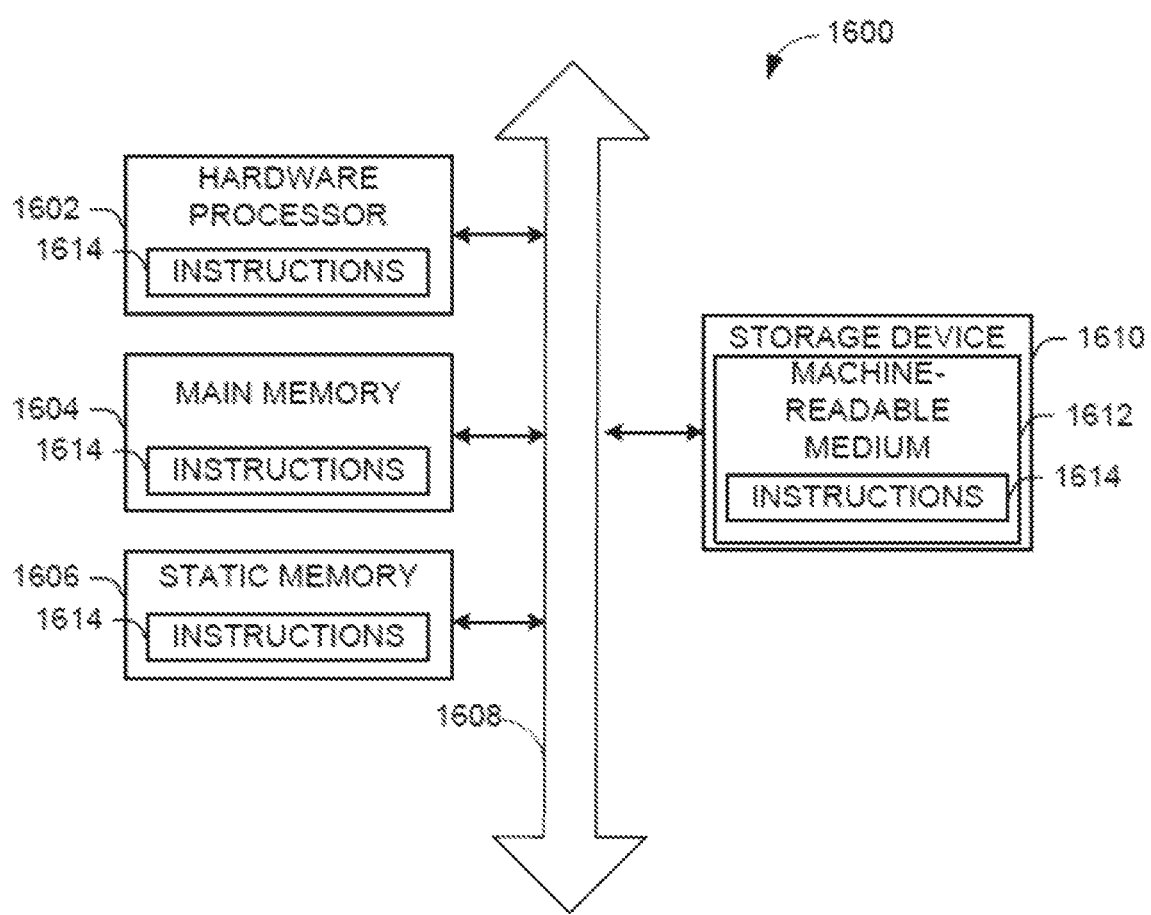
FIG. 16 shows a block diagram of an example device or system in accordance with embodiments of the present disclosure.

FIG. 16 illustrates a block diagram of an example of a device 1600 or system upon which any one or more of the techniques (e.g., methodologies) discussed herein may be performed. In other embodiments, the device 1600 may operate as a standalone device or may be connected (e.g., networked) to other devices. The device 1600 may be a personal computer (PC), a desktop computer, a mobile computer, a laptop computer, a notebook computer, a tablet computer, a server computer, a handheld computer, a handheld device, or any device capable of executing instructions (sequential or otherwise) that specify actions to be taken by that device. Further, while only a single device is illustrated, the term "device" shall also be taken to include any collection of devices that individually or jointly execute a set (or multiple sets) of instructions to perform any one or more of the methodologies discussed herein, such as cloud computing or other computer cluster configurations.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer-readable medium containing instructions where the instructions configure the execution units to carry out a specific operation when in operation. The configuring may occur under the direction of the execution units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

The device 1600 may include processing circuitry and memory arranged to perform the operations described herein. In some embodiments, the processing circuitry may be configured to perform operations detailed in FIGS. 14 and 15. In some embodiments, the processing circuitry of the device 1600 may include one or more processors. The memory may store information for configuring the processing circuitry to perform operations for performing the various operations described herein. The memory may include any type of memory, including non-transitory memory, for storing information in a form readable by a machine (e.g., a computer). For example, the memory may include a computer-readable storage device, read-only memory (ROM), random-access memory (RAM), magnetic disk storage media, optical storage media, flash-memory devices and other storage devices and media.

Certain embodiments may be implemented in one or a combination of hardware, firmware, and software. Other embodiments may also be implemented as instructions stored on a computer-readable storage device, which may be read and executed by at least one processor to perform the operations described herein. A computer-readable storage device may include any non-transitory memory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media. In some embodiments, the device 1600 may include one or more processors and may be configured with instructions stored on a computer-readable storage device memory.

The device (e.g., computer system) 1600 may include a hardware processor 1602 (e.g., a central processing unit (CPU), a hardware processor core, or any combination thereof), a main memory 1604 and a static memory 1606, some or all of which may communicate with each other via an interlink (e.g., bus) 1608. The device 1600 may further include a storage device (i.e., drive unit) 1610. The storage device 1610 may include a machine-readable medium 1612 on which is stored one or more sets of data structures or instructions 1614 (e.g., software) embodying or utilized by any one or more of the techniques or functions described herein. The instructions 1614 may also reside, completely or at least partially, within the main memory 1604, within the static memory 1606, or within the hardware processor 1602 during execution thereof by the device 1600. In an example, one or any combination of the hardware processor 1602, the main memory 1604, the static memory 1606, or the storage device 1610 may constitute machine-readable media. While the machine-readable medium 1612 is illustrated as a single medium, the term "machine-readable medium" may include a single medium or multiple media (e.g., a centralized or distributed database, and/or associated caches and servers) configured to store the one or more instructions 1614.

Various embodiments may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read-only memory (ROM), random access memory (RAM), magnetic disk storage media, optical storage media, a flash memory, etc.

The term "machine-readable medium" may include any medium that is capable of storing, encoding, or carrying instructions for execution by the device 1600 and that cause the device 1600 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., electrically programmable read-only memory (EPROM), or electrically erasable programmable read-only memory (EEPROM)) and flash memory devices;

magnetic disks, such as internal hard disks and removable disks; magneto-optical disks; and CD-ROM and DVD-ROM disks.

Certain aspects of the disclosure are described above with reference to block and flow diagrams of systems, methods, apparatuses, and/or computer program products according to various implementations. It will be understood that one or more blocks of the block diagrams and flow diagrams, and combinations of blocks in the block diagrams and the flow diagrams, respectively, may be implemented by computer-executable program instructions. Likewise, some blocks of the block diagrams and flow diagrams may not necessarily need to be performed in the order presented, or may not necessarily need to be performed at all, according to some implementations.

These computer-executable program instructions may be loaded onto a special-purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable storage media or memory that may direct a computer or other programmable data processing apparatus to function in a particular manner, such that the instructions stored in the computer-readable storage media produce an article of manufacture including instruction means that implement one or more functions specified in the flow diagram block or blocks. As an example, certain implementations may provide for a computer program product, comprising a computer-readable storage medium having a computer-readable program code or program instructions implemented therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, may be implemented by special-purpose, hardware-based computer systems that perform the specified functions, elements or steps, or combinations of special-purpose hardware and computer instructions.

Many modifications and other implementations of the disclosure set forth herein will be apparent having the benefit of the teachings presented in the foregoing descriptions and the associated drawings. Therefore, it is to be understood that the disclosure is not to be limited to the specific implementations disclosed and that modifications and other implementations are intended to be included within the scope of the appended claims. Although specific terms are employed herein, they are used in a generic and descriptive sense only and not for purposes of limitation.

Specific Examples

Suitability of IMS-MS for Elucidating Molecular Structures

Native protein structures need to be retained in the gas phase long enough, while sufficiently maintaining structural integrity of the protein, in order to ensure confident and accurate protein structure elucidation from IMS-MS data. Data indicates that cooperativity between protein substructures can prevent protein denaturation in the gas phase for at least up to several seconds. It is possible to assess how closely IMS-MS data reflects the native state of proteins by comparing unfolding rate constants measured by time-resolved IMS-MS to those measured by solution techniques for variants of a protein.

FIG. 3 shows results of efforts for advancing TIMS-MS for use in structural biology. These efforts led to a fundamental understanding of the measurement and time-resolved ion trapping processes, the ability to measure cross sections without calibration, and the ability to study structure and reactivity of proteins.

IMS-MS Instrument

Figure 2:
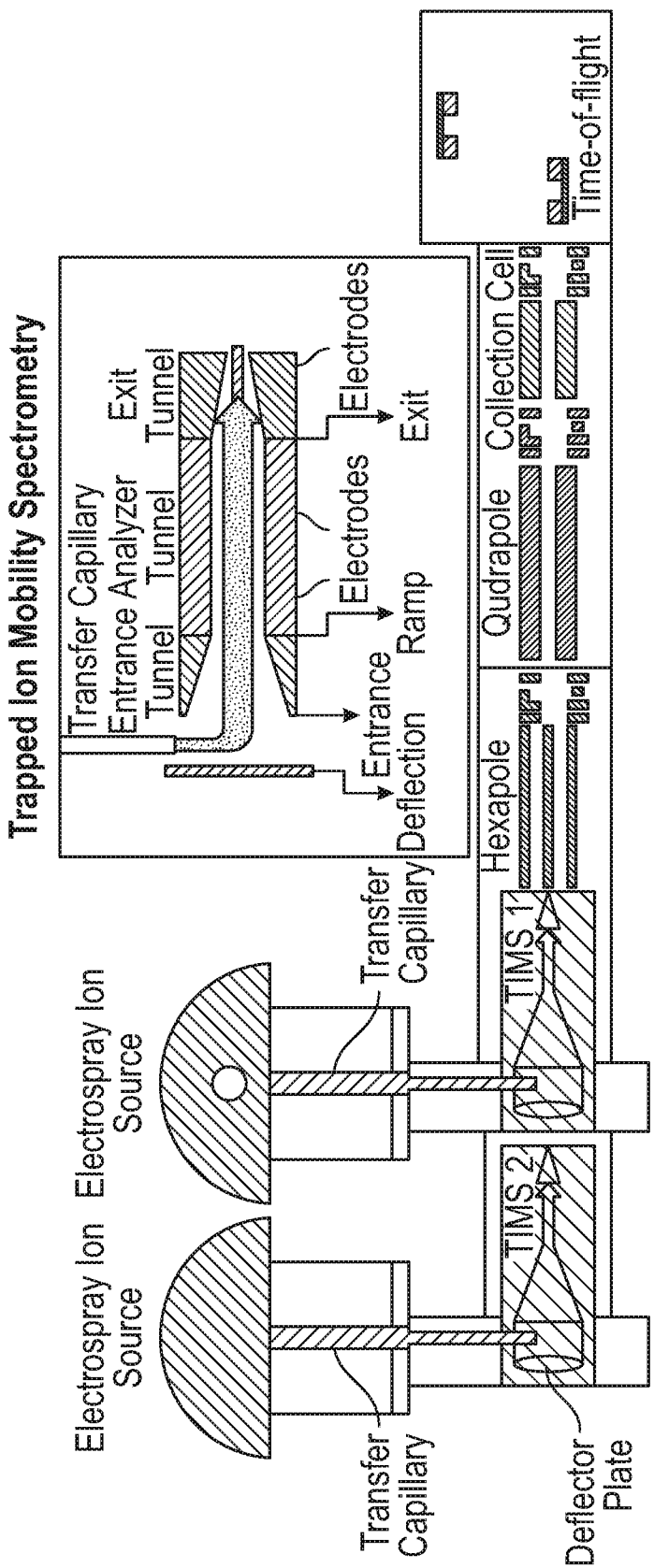
FIG. 2 shows an IMS-MS instrument suitable for use in accordance with embodiments of the present disclosure.
Figure 3A:
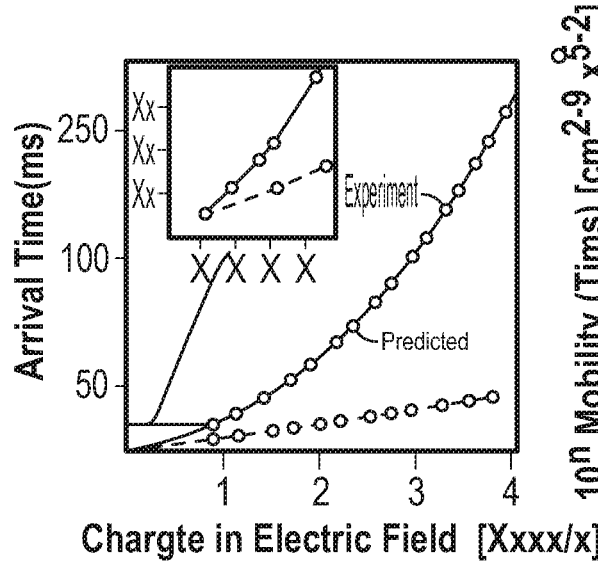
FIGS. 3A-3D show various experimental results.
Figure 3B:
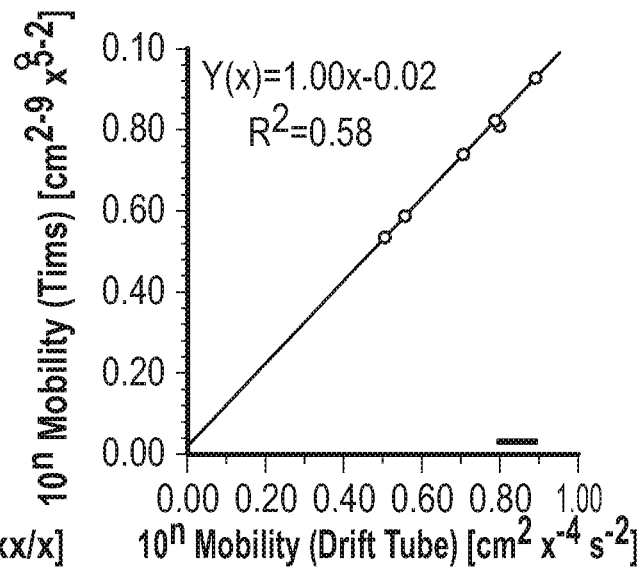
Figure 3C:
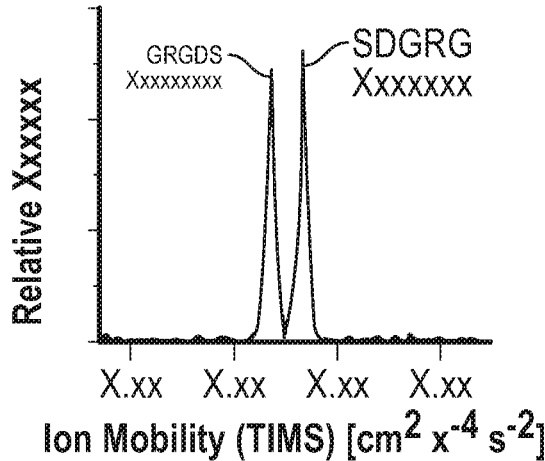
Figure 3D:
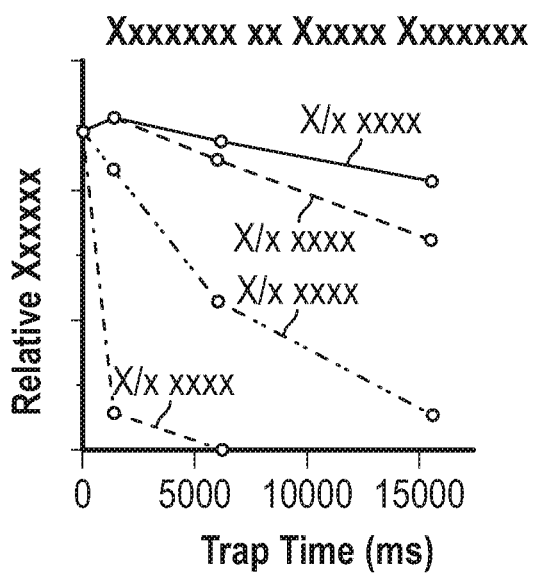
Figure 4:
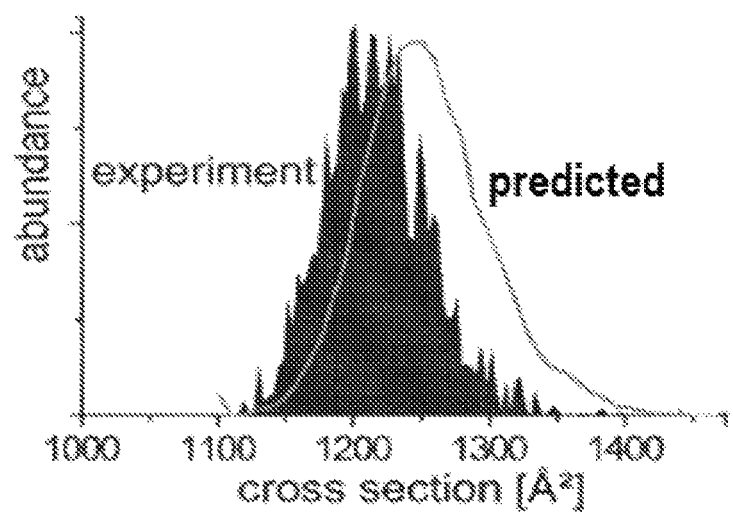
FIG. 4 shows measured and predicted IMS-MS spectra for the chemokine CCL5 (6+ charge state). The systems and methods of the present disclosure elucidated fundamental aspects of how oligomeric chemotactic cytokines (chemokines) control migration of immune cells.

IMS-MS measurements can be carried out on a trapped IMS-MS (TIMS-MS) platform. A major advantage of TIMS-MS over other IMS-MS systems is its much higher resolution. The TIMS-MS provides time-resolved measurements for up to 15 s. FIG. 2 shows a dual-stage TIMS-MS system suitable for use in accordance with embodiments of the present disclosure.

Methods for Determining Molecular Cross Sections

The PSA and LCPA methods predict cross sections in different buffer gases accurately and efficiently, as illustrated in FIG. 1. Hence, these methods are decisive for de novo protein structure elucidation by IMS-MS. The PSA and LCPA algorithms employed for cross section calculations are as accurate as the trajectory method (TJM) but much faster. Projection approximations are inaccurate (~30% error).

Ubiquitin as a Model Molecule

The present disclosure quantitatively assessed how closely computed IMS-MS data for the protein ubiquitin reflected the native state of ubiquitin (e.g. solution structures of ubiquitin). This was done in order to test whether the systems and methods of the present disclosure could accurately elucidate protein structures from IMS-MS data and provide a means to extract biologically relevant information from IMS-MS data.

The present disclosure stems, in part, from the understanding that biologically relevant structures can be retained in an IMS-MS experiment for at least several seconds due to cooperativity between different protein substructures. Using ubiquitin as a model molecule, the present disclosure investigated kinetics and mechanisms for unfolding of ubiquitin variants by time-resolved measurements using a trapped IMS-MS platform and compared these results to unfolding in solution (i.e. φ-value analyses).

In order to study biological processes that occur in solution under physiological conditions, IMS-MS determines native structures of proteins present in solution. These native protein structures often comprise a hydrophobic core and a hydrophilic surface. However, IMS-MS methods measure cross sections of proteins in the gas phase, where proteins favor hydrophilic cores and hydrophobic surfaces. Some aspects of native protein structures can be kinetically trapped on "soft" IMS-MS instruments. For low charge states, ubiquitin cross sections recorded on "soft" drift-tubes agree with NMR structures.

Figure 5:
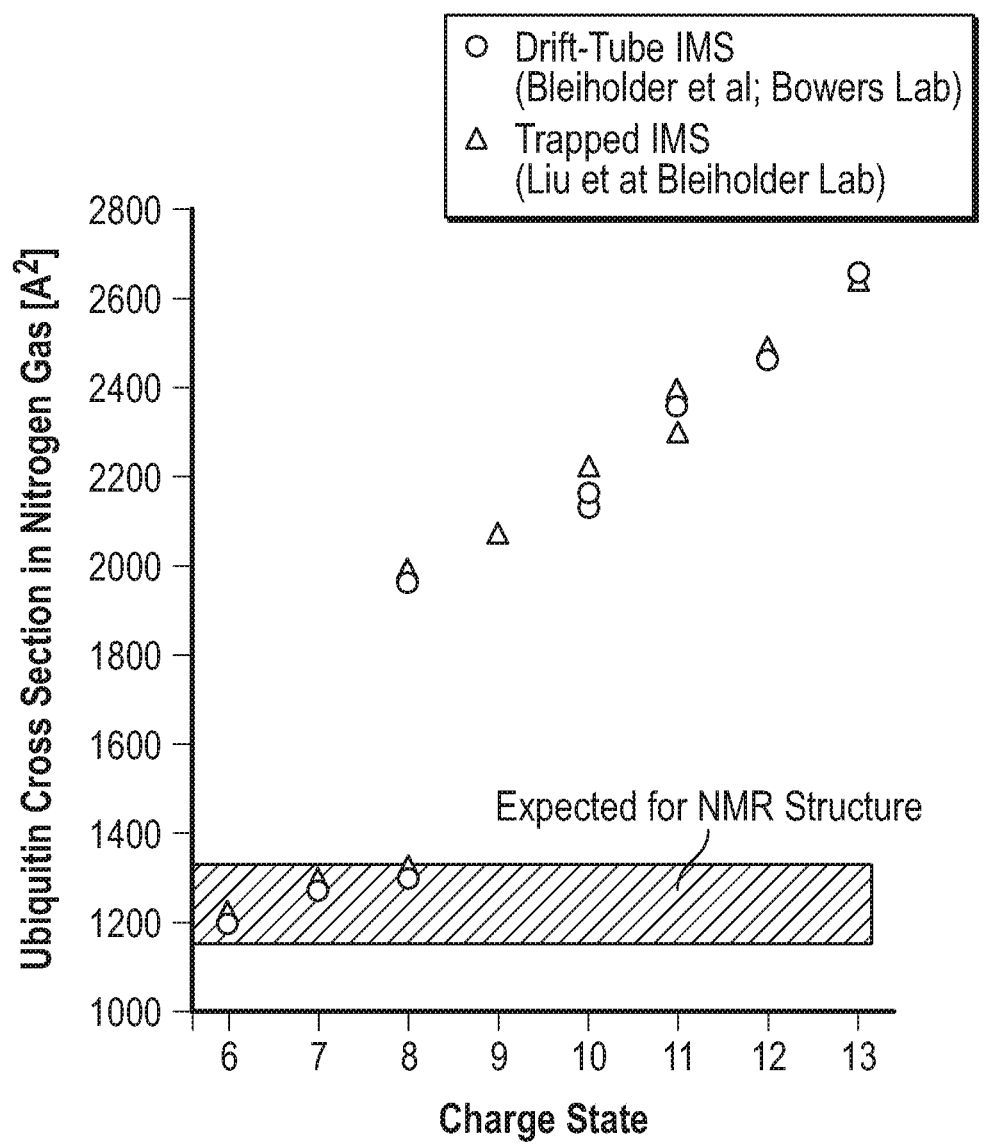
FIG. 5 shows cross sections of ubiquitin for various charge states, wherein IMS-MS data (triangles) reproduce Bowers' data (circles), and wherein cross sections of low charge states agree with the NMR structure.

It has been shown that a modified TIMS-MS instrument reproduces drift-tube data and that cross sections for low charge states agree with the NMR structure, as illustrated in FIG. 5. The present systems and methods can trap and structurally characterize ubiquitin ions in the exact same location as in the time-resolved TIMS-MS measurements. The present systems and methods can quantitatively analyze time-resolved IMS-MS spectra and a TIMS-MS instrument in accordance with the present disclosure can allow for the study of protein unfolding in the gas phase for up to 15 s at IMS resolving powers exceeding ~200.

Figure 6A:
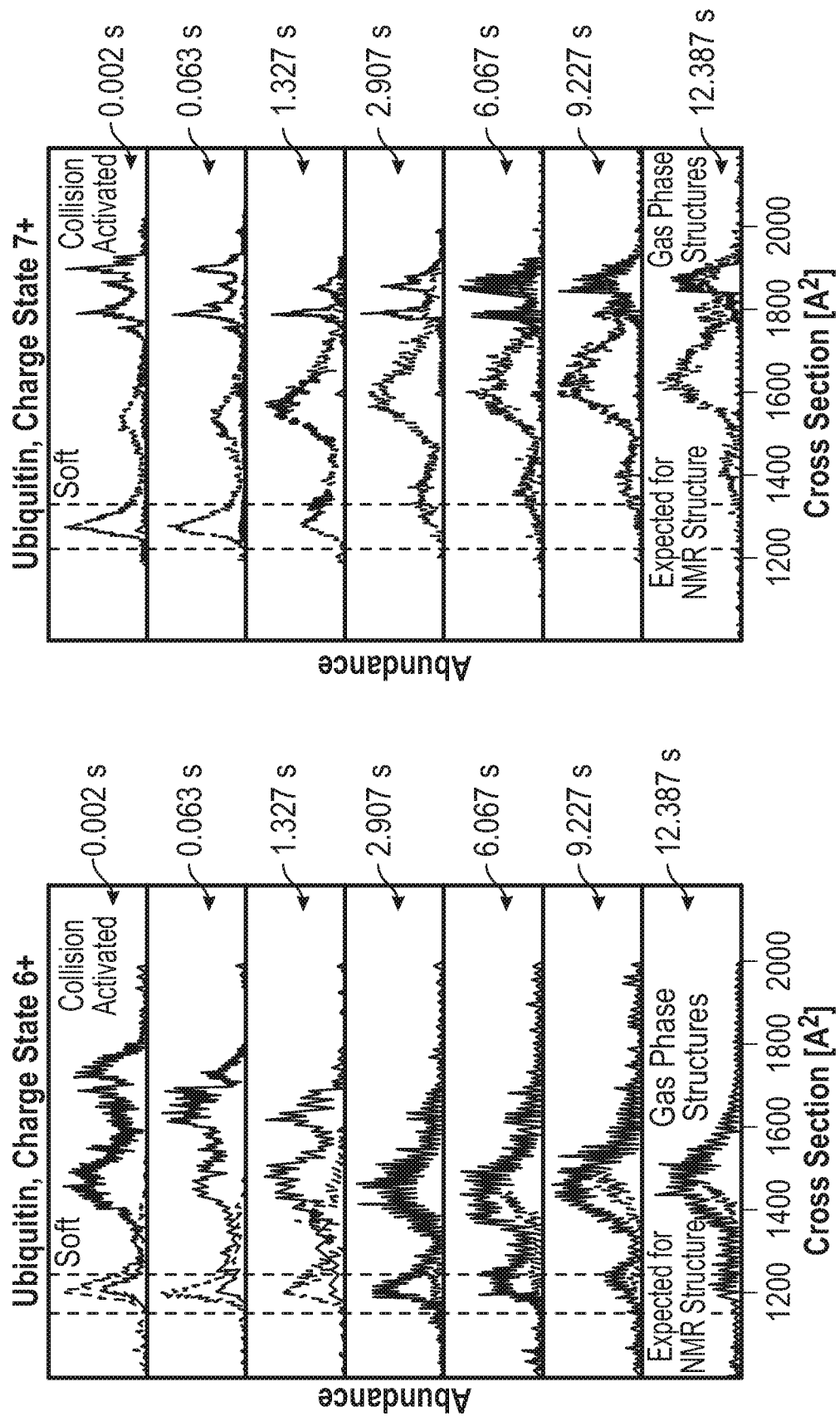
FIGS. 6A-6B show experimental results for the protein ubiquitin.

Time-resolved IMS-MS spectra, as shown in FIG. 6A, illustrates that native-like features of ubiquitin are stable on the timescale of seconds. Rate constants for unfolding are ~0.16 s−1 (6+) and ~0.20 s−1 (7+), underscoring the ability of the present disclosure's setup in retaining native-like protein structures. These rate constants qualitatively agree with measurements conducted in solution. Additionally, for charge state 7+, it is observed that collisionally-activated conformations refold into compact structures, followed by subsequent unfolding into species that differ ~1% in cross section from the initial conformations. This observation is important because it shows that IMS≥100 are generally needed to accurately probe the dynamics of biological analytes in IMS-MS experiments. Such IMS resolving powers are routinely achieved in the systems and methods of the present disclosure, but not typically in other systems currently known in the art. Thus, the data show that the IMS-MS systems of the present disclosure are able to probe protein dynamics in the absence of solvent for extended periods of time at high resolving power under "soft" conditions.

Figure 6B:
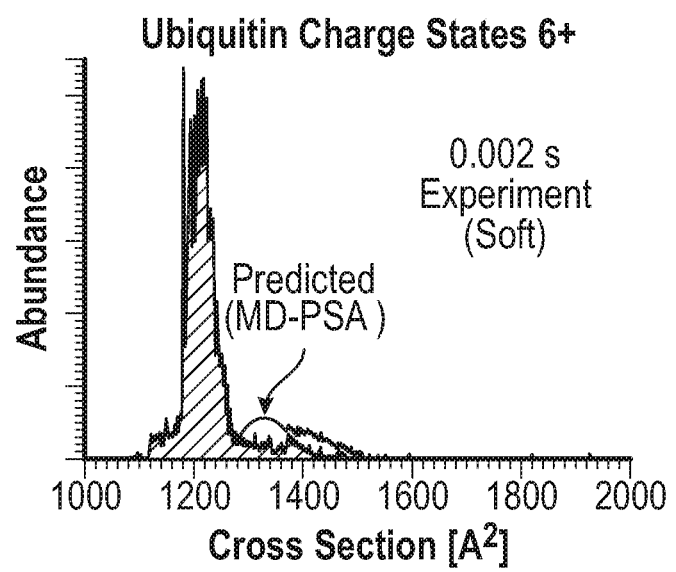
Figure 6B:
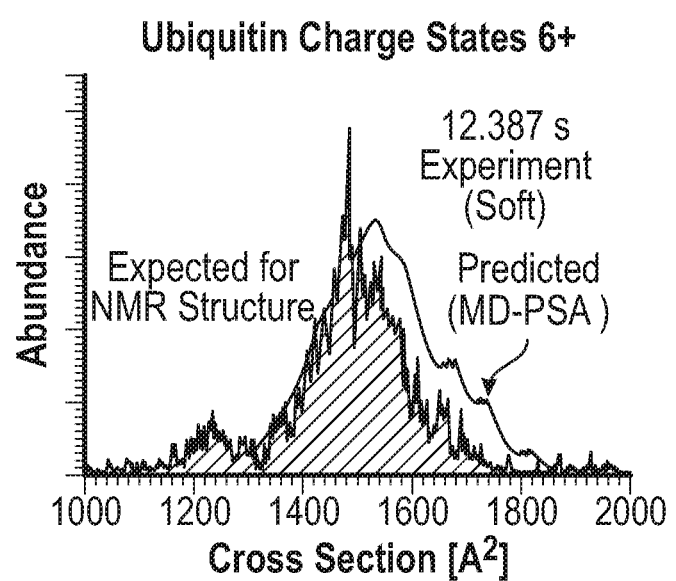

In an exemplary embodiment, the systems and methods of the present disclosure predicted time-resolved IMS-MS spectra for each charge state of ubiquitin to identify the changes in protein structure probed by time-resolved IMS-MS experiments, shown for 6+ in FIG. 6B, as opposed to comparing individual cross section values for specific structures times.

In embodiments, the systems and methods of the present disclosure predicted IMS-MS spectra for ubiquitin, starting by conducting explicit solvent molecular dynamics (MD) simulations based on ubiquitin NMR structures. The MD simulations address protein dynamics in the gas phase. Thousands of structures from the solution simulations were considered and all charge states were explicitly handled. PSA and LCPA methods were then used to calculate cross sections at various steps during the unfolding trajectories for correlation to time-resolved IMS-MS experiments. PSA and LCPA methods were used because these two methods are accurate and computationally efficient.

Figure 7:
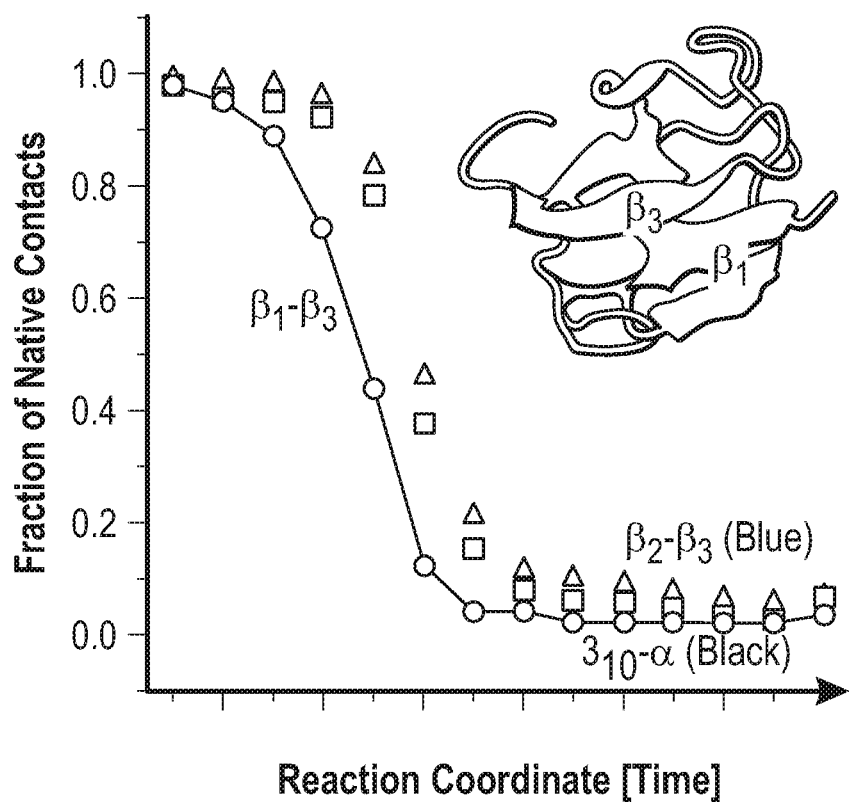
FIG. 7 shows a proposed unfolding mechanism of ubiquitin 6+, as determined in part by IMS-MS data. The unfolding starts when the interaction between the two central β-strands is lost, as revealed by native contacts as a function of time.

As illustrated in FIG. 6B, predicted time-resolved spectra for ubiquitin charge state 6+ match the experiment closely, thereby once again establishing agreement between predicted and experimental structures. This allowed for revealing the unfolding mechanism in the experiment. How native contacts change during the gas phase simulations can be analyzed, as illustrated in FIG. 7. The data indicates that denaturation of ubiquitin in the gas-phase is initiated when the interaction between the N- and C-terminal β-strands is lost. This observation shows that cooperativity between distinct ubiquitin substructures impedes denaturation in the gas phase.

It can be determined how closely related cooperative effects in the gas and solution phase are by comparing the respective unfolding rate constants and mechanisms for ubiquitin mutants as follows:

(i) Protein model systems use ubiquitin as a model system because it has been exhaustively characterized by a number of experimental and theoretical techniques including ϕ-value analyses, and kinetic studies have been performed. Specifically, ubiquitin mutants are selected from a ϕ-value analysis and all variants are studied with ϕ-values of ~1.0 (D21N, A28G, I23A, I23G) and selected mutations with fractional ϕ-values (Nterminal region, VSA, T7A, I13A, L15A, V17A) and ϕ-values of approximately zero (C-terminal region, Q41A, L43A, L50A, I61A). Wild-type (WT) ubiquitin can be obtained from AddGene.org (Plasmid #12647). Ubiquitin variants can be produced in BL21/DE3 *E. coli* grown at 37° C. on either rich LB medium or minimal M9 medium and purified by $Ni^{2+}$-affinity chromatography and other chromatographic polishing steps. This can be used to provide ubiquitin variants for time-resolved IMS-MS measurements.

(ii) Unfolding kinetics can be determined from time-resolved IMS-MS spectra as described (FIG. 6A) for 1-10 μM samples. Regression analysis can extract unfolding rate constants from the time-resolved data. Each ubiquitin variant is expected to exhibit a distinct rate constant.

(iii) Charge-state specific dynamics of ubiquitin in the gas-phase can be simulated as described (FIG. 6B) for each variant studied under (ii). Initial structures can be constructed from NMR and x-ray structures of WT ubiquitin by modifying residues. MD simulations can be conducted for 100 ns as described. Snapshots from these simulations can be used to carry out gas-phase MD simulations as described, but for each charge state and with the OPLS force field as justified by preliminary data (FIG. 6B). To attain distinct charge states, amino acid residues are (de)protonated based upon electrostatic potential calculations with the semi-empirical AM1 Hamiltonian.

(iv) Prediction of IMS-MS spectra by the PSA algorithm. Collision cross sections can be calculated by the PSA method to predict IMS-MS spectra for structural analysis of the experiment (FIG. 6B). Specifically, PSA calculations can be carried out for each initial and final structure obtained from each gas-phase unfolding trajectory and protonation state under (iii). Structures can be clustered based on the gas-phase MD simulations from step (iii). The average PSA cross section for each cluster is weighted by the population of this cluster. This approach is justified by data (FIG. 6B).

(v) Mechanistic interpretation of the unfolding process can be conducted as described (FIG. 7) once agreement between experimental and predicted spectra is established (FIG. 6B). Changes in hydrophilic and hydrophobic surface areas, computed as described, can identify globular structural changes during unfolding. Changes in native contacts can identify (1) the overall degree of denaturation of ubiquitin, (2) the relative stability of the ubiquitin substructures in the gas-phase, and (3) the strength of the interaction between different substructures (FIG. 7).

Step (ii) can determine unfolding rate constants in the gas phase for the ubiquitin variants expressed in (i). The ubiquitin variants exhibit distinct unfolding rate constants. These gas-phase unfolding rate constants can be compared to the corresponding unfolding rate constants measured in solution. Unfolding rates in solution and IMS-MS can be positively and linearly correlated if unfolding in solution and in IMS-MS are equivalent. Deviations from this expected correlation can identify differences between structures and unfolding transition states in solution and in IMS-MS. The different mutations can reveal these differences at a residue-specific level. Activities in steps (iii) to (v) determine the unfolding mechanism of various ubiquitin systems in TIMS-MS (FIG. 6B and FIG. 7). This analysis can identify which substructures of the ubiquitin variants are more prone to unfolding than others, and, additionally, which interactions between the various substructures remain native-like longer than others (FIG. 7). In sum, the systems and methods of the present disclosure can identify the influence of solvent on cooperative effects in ubiquitin, and thus how closely IMS-MS data reflect the native state of ubiquitin. This knowledge can be used to confidently elucidate protein structures with IMS-MS.

The systems and methods of the present disclosure are effective in identifying how closely IMS-MS data reflect the native state of ubiquitin. The systems and methods of the present disclosure can also be generally applied to other molecules, including intrinsically disordered proteins (IDPs), protein oligomers, or membrane protein receptors. Phi-value analyses have been performed for IDPs (e.g. the acetylcholine receptor). Studying these molecules can be important because IDPs and their oligomers are implicated in Alzheimer's and other amyloid diseases while membrane protein receptors are important but notoriously difficult to study by traditional means.

Figure 8:
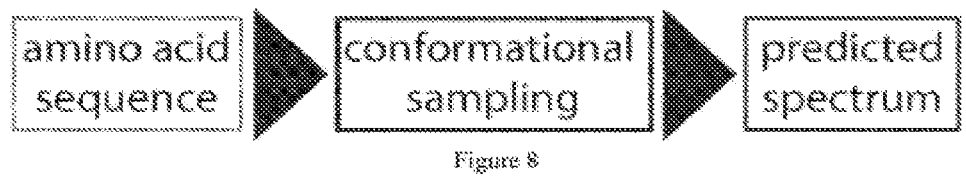
FIG. 8 shows a flowchart for predicting a molecule's three-dimensional structure from time-resolved IMS-MS spectra considering only the Lewis structure (e.g. amino acid sequence) of the molecule (e.g. a protein).

In embodiments, the present disclosure provides an automated software algorithm for IMS-MS data analysis in order to enable de novo protein structure elucidation. In embodiments, the systems and methods of the present disclosure do not use a conformational search based on known NMR or x-ray structures but instead use a comprehensive conformational search that is free of such bias, as shown in FIG. 8.

Figure 9:
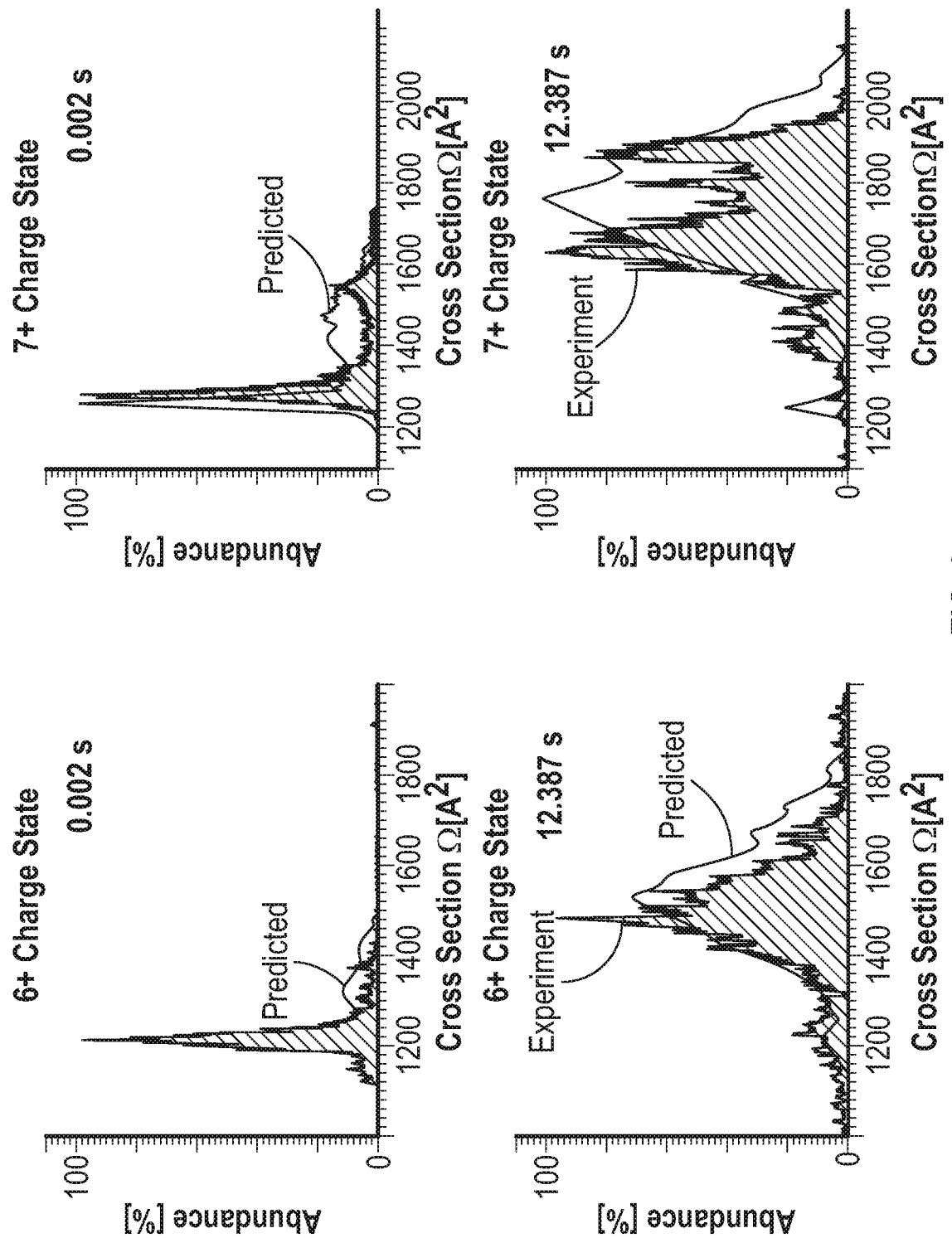
FIG. 9 shows predicted and measured time-resolved IMS spectra (ubiquitin, charge states 6+, 7+, 8+). Native-like peaks are present at 0.002 s under "soft" settings. The experimental and predicted time-resolved IMS-MS spectra strongly agree, demonstrating that the systems and methods of the present disclosure can quantitatively and unambiguously interpret IMS-MS spectra for molecules (e.g. proteins).
Figure 9:
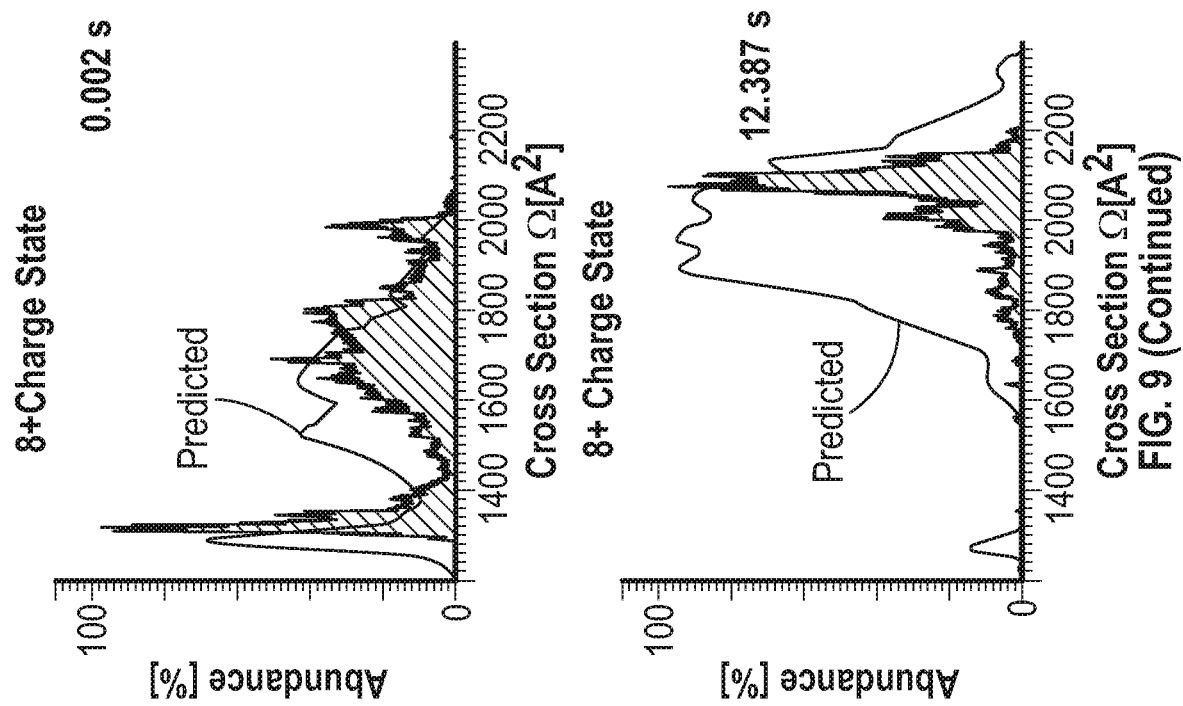
Figure 10:
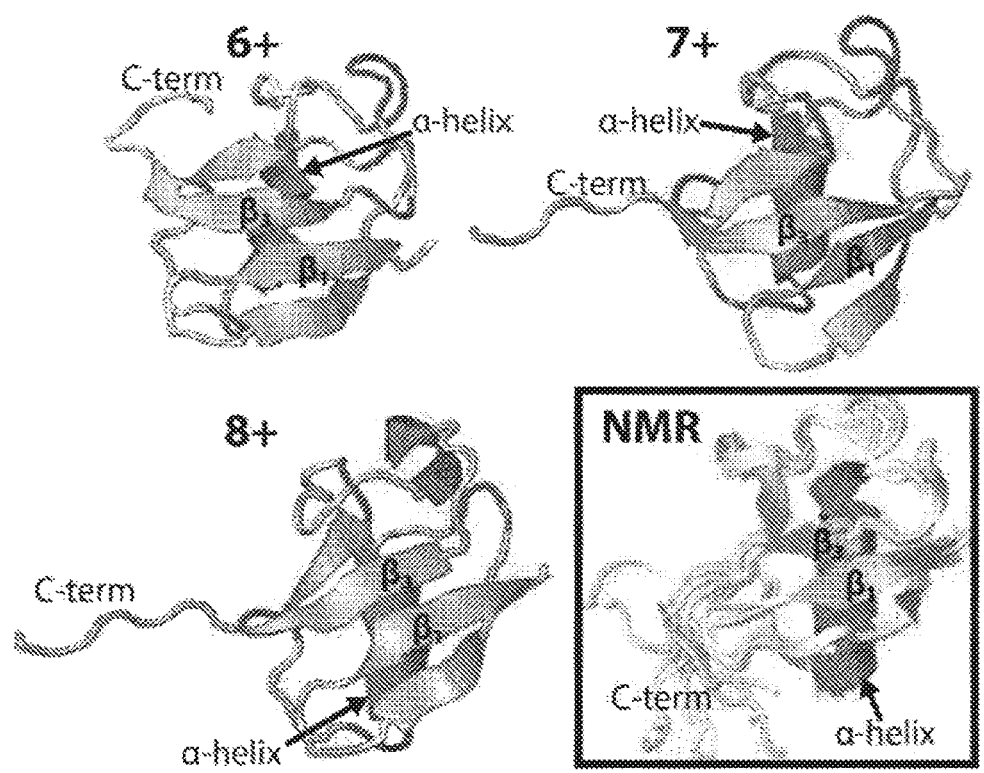
FIG. 10 shows a comparison between ubiquitin's structure as determined by NMR and the most populated clusters predicted, in accordance with embodiments of the present disclosure, for the compact peaks (~1200-1300 Å$^2$) of charge states 6+, 7+, 8+. The IMS-MS and NMS structures agree in terms of secondary and tertiary structure. Therefore the methods and systems of the present disclosure can accurately elucidate tertiary structures of molecules (e.g. proteins) de novo (i.e. using only IMS-MS data).
Figure 11:
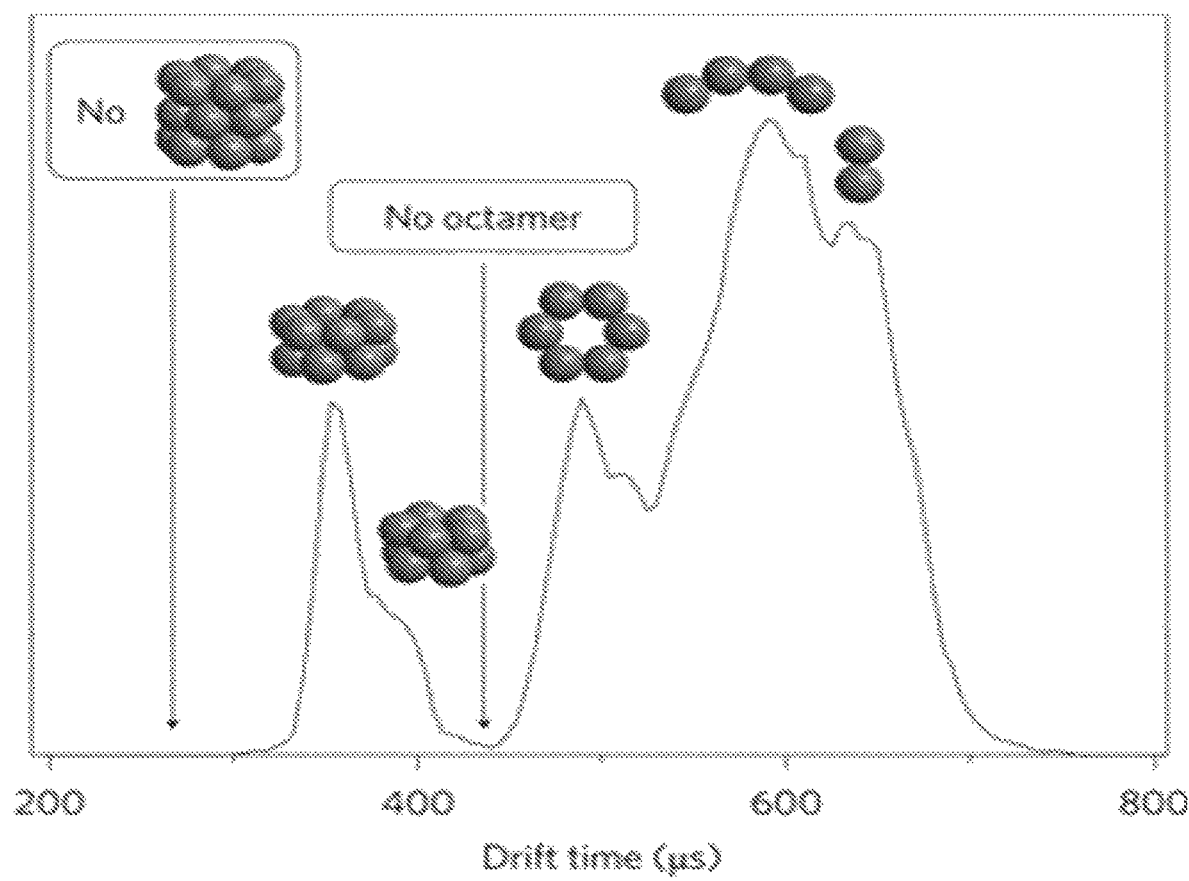
FIG. 11 shows that IM-MS reveals prion-like assemblies of Aβ peptides implicated in AD. Structural details (e.g. how subunits are bound) are not amenable to study using conventional techniques. The present systems and methods are able to identify how peptides assemble from individual monomers into amyloid fibrils, a key step in the onset of AD. This provides, among other things, a molecular mechanism for AD drug candidates.

The present systems and methods were used to predict time-resolved IMS-MS spectra for various ubiquitin charge states based on ubiquitin NMR structures. Comparison of time-resolved experimental and predicted spectra, as illustrated in FIG. 8, shows close agreement. The data show that the computational procedure of the present disclosure accurately predicts time-resolved, charge-state specific IMS-MS spectra for proteins as long as the initial conformational search samples native structures. Additionally, the time-resolved IMS-MS spectra reveal that the compact peaks (~1200-1300 Å2) in the initial experimental spectra reflect native-like protein conformations because the entire protein unfolding process is monitored. The experimental data shows that those conformations that bring about the compact "native" peaks in the predicted spectra (FIG. 9) are (1) highly similar for all three charge states and (2) closely match the ubiquitin NMR structure in terms of secondary and tertiary structure, as shown in FIG. 10. Hence, native structures of other proteins can be identified with the workflow provided by the present disclosure as long as the initial conformational search (FIG. 8) samples native conformations.

Exemplary Method for De Novo Molecular Structure Determination

In accordance with an exemplary embodiment of the present invention, molecular structures can be identified de novo by:

(i) Measuring time-resolved TIMS-MS spectra and using the time-resolved spectra to identify "native peaks."

(ii) Performing a comprehensive, unbiased conformational search from knowledge of the target chemical structure. This step can produce a large number (>5000) candidate structures for further analysis.

(iii) Ionizing (e.g. protonate or deprotonate) candidate structures produced under (ii) to attain all charge states used as experimental input from step (i). For each experimental charge state used as input, this step can produce a unique charge state for each candidate structure produced under (ii).

(iv) Relaxing the charged structures in the gas phase by MD simulations. Snapshots are saved for analysis every 20 ps. Prior experience shows that this approach accurately accounts for charge-state specific molecular dynamics in the gas phase. These calculations can be performed for each structure obtained from steps (ii) and (iii).

(v) Predicting time-resolved IMS spectra on the basis of the PSA cross sections for the trajectories obtained from step (iv). This step predicts charge-state specific IMS spectra for comparison to the experiment recorded in step (i).

(vi) Measuring similarity between predicted and experimental ion mobility spectra by means of cross correlation. This approach is justified as the data indicates that peaks in the predicted spectra are mainly shifted by a value $\delta\Omega$ with respect to the experiment. Similarity scoring can calculate the shift in cross section $(\delta\Omega)$max that maximizes the cross correlation $xi(\delta\Omega)=Ei*Pi$ between experimental and predicted spectra, Ei and Pi, respectively:

$$X(\delta\Omega) = \sum_{i}^{spectra} x_i(\delta\Omega) = \sum_{i}^{spectra} (E_i * P_i)(\delta\Omega)$$

(vii) Iteratively optimizing predicted IMS spectra if the scored shift in cross section $(\delta\Omega)$max between predicted and experimental spectra is below a user-defined threshold. To this end, steps (v) and (vi) can be iteratively repeated after removing outlying structures from the predicted spectra until the desired threshold is attained. This step identifies the subset of the initial structures (e.g. >5000) from step (i) that best explain the experimental IMS-MS data.

(viii) Identifying molecular structures on the basis of a cluster analysis of the structures identified in step (vii). Such structures will reflect native protein structures (FIG. 10).

Exemplary Method for De Novo Molecular Assembly Determination

Figure 12:
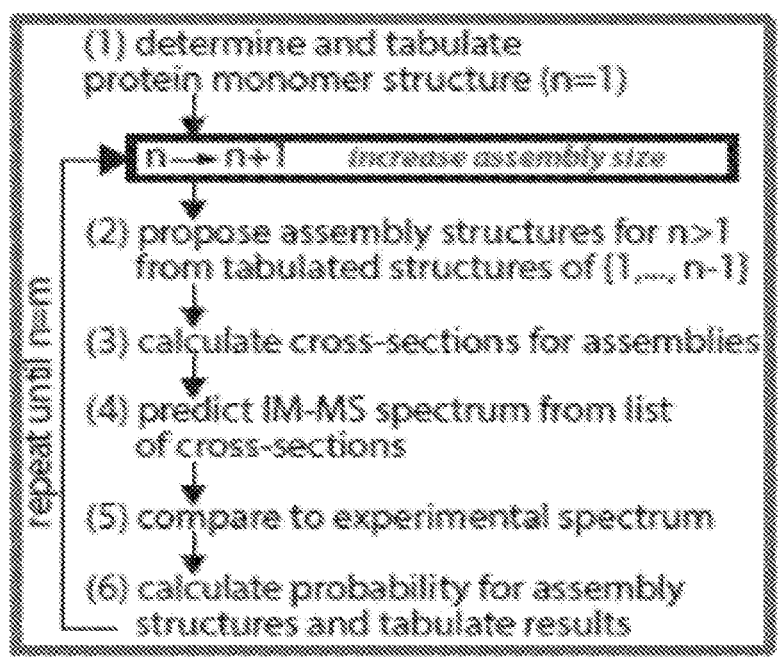
FIG. 12 shows a workflow to determine detailed structures of molecular assemblies (e.g. protein assemblies) with IMS-MS in accordance with embodiments of the present disclosure.

In embodiments, the present disclosure provides a software algorithm that determines structures of protein assemblies from IM-MS data. In embodiments, the systems and methods of the present disclosure can be adapted from a dynamic programming algorithm to calculate Fibonacci numbers (see FIG. 12). The initial step is to determine and tabulate structures of the protein monomers (n=1). The strategy then is to iteratively combine tabulated structures of smaller species {1, . . . , n−1} into larger assemblies (n>1) until the desired assembly is reached (n=m). For example, tabulated monomer structures (n=1) are combined into dimers (n=2; 2=1+1). Then, trimers (n=3) are built from three monomers (3=1+1+1) as well as from monomers and dimers (3=2+1). Tetramers (n=4) are built from combining monomers, dimers, trimers, etc.

The systems and methods of the present disclosure can (1) identify structures of protein monomers from IM-MS data; (2) propose (thousands of) structures of protein assemblies from combining smaller species; (3) calculate collision cross sections for these assemblies; (4) predict IM-MS spectra from the set of calculated cross-sections; (5) cross-correlate experimental and predicted IM-MS spectra for (6) probability ranking of the assembly structures and tabulating of the results.

Figure 13:
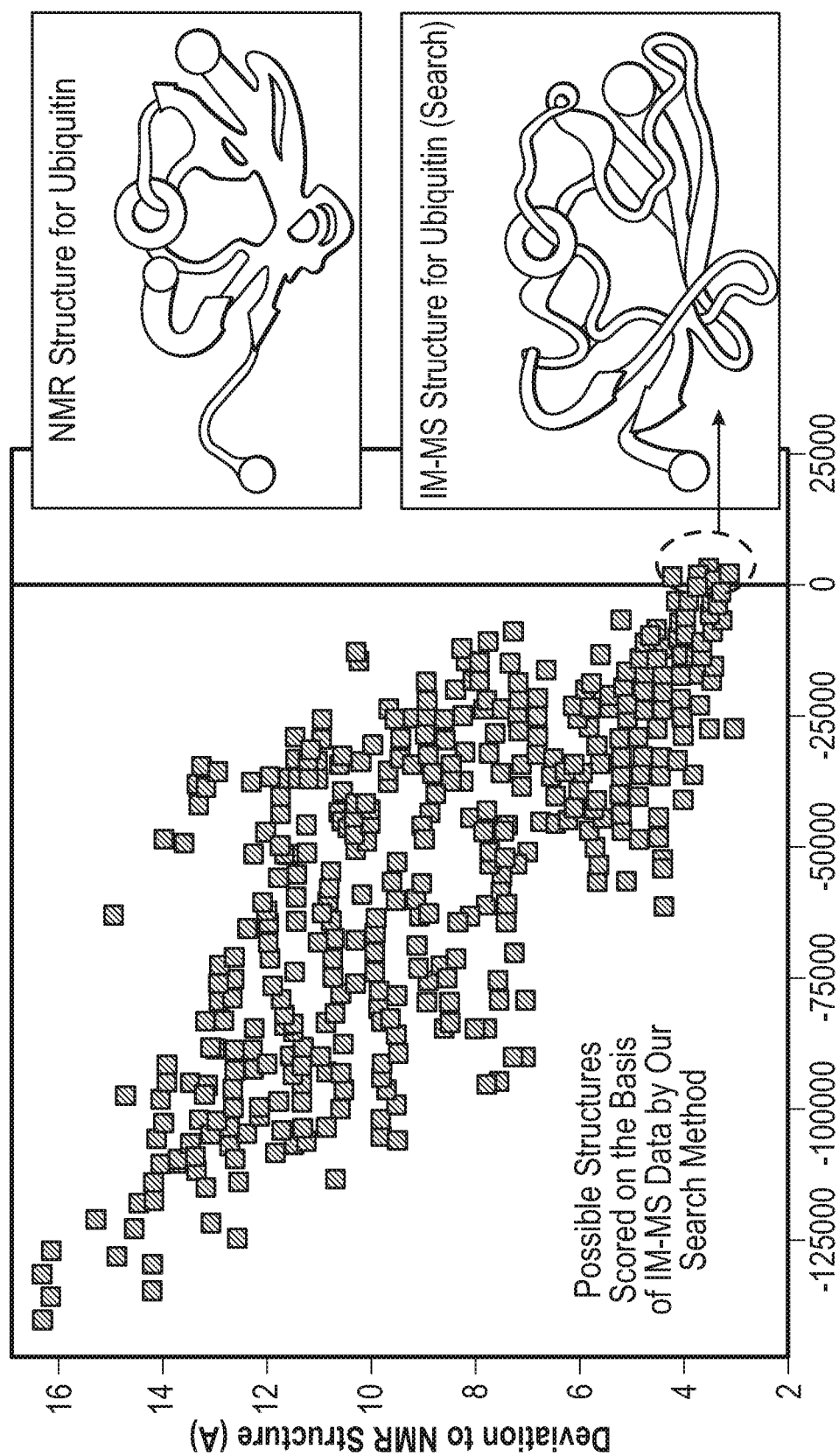
FIG. 13 shows that protein structures revealed from IM-MS by the SEARCH method match NMR structures.

Step (1), identify structures of protein monomers from IM-MS data, can be conducted by the Structure Elucidation by Analysis of Restraints from Cross-correlation of Histograms (SEARCH) algorithm (FIG. 13). The SEARCH algorithm can determine structures of protein monomers from IM-MS data. In step (2), protein docking methods (e.g. ZDOCK, HADDOCK) can be used to predict assembly structures. Step (3) can be carried out using the LCPA method. Steps (4) to (6) can be adopted from the SEARCH algorithm. The systems and methods of the present disclosure can elucidate structures of molecules having 0-2,000 atoms, 0-30,000 atoms, and structures having greater than 30,000 atoms.

The invention claimed is:

1. A method for determining a molecular structure of a molecule or a molecular structure of a molecular assembly, the method comprising:
   [a] determining, based on a Lewis structure of a molecule, a plurality of candidate molecule structures of the molecule, or [b] determining, for a molecule, a plurality of candidate molecular assemblies;
   determining a predicted time-resolved ion mobility mass spectrometry (TRIM-MS) spectrum for each of the candidate molecule structures or candidate molecular assemblies;
   determining, based at least in part on a measure of similarity between a measured TRIM-MS spectrum of the molecule or the molecular assembly of the molecule and each of the predicted TRIM-MS spectra, a subset of candidate molecule structures or candidate molecular assemblies;
   determining a candidate score for each candidate molecule structure or candidate molecular assembly in the subset; and
   assigning, based on the candidate scores, a molecular structure of the molecule or a molecular assembly of the molecule.

2. The method of claim 1, wherein determining the plurality of candidate molecule structures comprises:
   determining, based on the Lewis structure of the molecule, a plurality of initial candidate structures using an unbiased conformational search;
   determining an ionized candidate structure for each of the initial candidate structures, wherein each of the ionized candidate structures have a same charge state; and
   determining, by relaxing each of the ionized candidate structures in a molecular dynamics simulation, the candidate molecule structure for each of the ionized candidate structures.

3. The method of claim 1, wherein determining the plurality of candidate molecular assemblies comprises:
   docking, by a macromolecular docking algorithm, one or more of the molecule, one or more assemblies of the molecule, or a combination thereof, with one another to form the plurality of candidate molecular assemblies.

4. The method of claim 1, wherein determining the predicted TRIM-MS spectra for each of the candidate molecule structures or each of the candidate molecular assemblies comprises:
   determining collision cross sections for each of the candidate molecule structures or candidate molecular assemblies; and
   determining, based on the collision cross sections, the predicted TRIM-MS spectra for each of the candidate molecule structures or candidate molecular assemblies.

5. The method of claim 4, wherein the collision cross sections for each of the candidate molecule structures or each of the candidate molecular assemblies is determined by projection superposition approximation (PSA) or local collision probability approximation (LCPA).

6. The method of claim 1, wherein the subset of candidate molecule structures or the subset of candidate molecular assemblies is each candidate molecule structure or each candidate molecular assembly, respectively, whose corresponding predicted TRIM-MS spectra, when shifted by a $\delta\Omega$ value, overlaps with the measured TRIM-MS spectrum.

7. The method of claim 1, wherein [a] determining the candidate score for each candidate molecule structure in the subset comprises:
   determining, for each candidate molecule structure in the subset, an atom-atom distance probability distribution for each atom-atom pair; and
   determining, for each candidate molecule structure in the subset, the candidate score based on a joint probability based on the atom-atom distance probability distribution for each atom-atom pair;
   and [b] determining the candidate score for each candidate molecular assembly in the subset comprises:
   cross-correlating the measured TRIM-MS spectrum of the molecular assembly of the molecule with each of the predicted TRIM-MS spectra; or
   determining a probability ranking for each candidate molecular assembly in the subset.

8. The method of claim 1, wherein assigning the molecular structure of the molecule or the molecular structure of the molecular assembly comprises:
   determining the molecular structure of the molecule or the molecular assembly is the candidate molecule structure or the candidate molecular assembly corresponding to a highest ranking candidate score.

9. The method of claim 1, further comprising creating a new data file or updating an existing data file for the molecule, the data file comprising:
   an identifier of the molecule; and
   the molecular structure of the molecule or the molecular structure of the molecular assembly.

10. The method of claim 1, further comprising providing the molecular structure of the molecule or providing the molecular structure of the molecular assembly by a process comprising:
    displaying an image of the molecular structure of the molecule or the molecular assembly, displaying coordinates of the molecular structure of the molecule or the molecular assembly, sending the image of the molecular structure of the molecule or the molecular assembly, sending coordinates of the molecular structure of the molecule or the molecular assembly, or a combination thereof.

11. A method for drug screening comprising:
    screening a potential therapeutic against the molecular structure of the molecule or the molecular assembly determined according to claim 1.

12. A device for determining a molecular structure of a molecule or a molecular structure of a molecular assembly, the device comprising memory and processing circuitry configured to:
    [a] determine, based on a Lewis structure of a molecule, a plurality of candidate molecule structures of the molecule, or [b] determine, for a molecule, a plurality of candidate molecular assemblies;
    determine a predicted time-resolved ion mobility mass spectrometry (TRIM-MS) spectra for each of the candidate molecule structures or candidate molecular assemblies;

determine, based at least in part on a measure of similarity between a measured TRIM-MS spectrum of the molecule or a molecular assembly of the molecule and each of the predicted TRIM-MS spectra, a subset of candidate molecule structures or candidate molecular assemblies;

determine a candidate score for each candidate molecule structure or candidate molecular assembly in the subset; and assign, based on the candidate scores, a molecular structure or a molecular assembly of the molecule.

13. The device of claim 12, wherein determining the plurality of candidate molecule structures comprises:

determine, based on the Lewis structure of the molecule, a plurality of initial candidate structures using an unbiased conformational search;

determine an ionized candidate structure for each of the initial candidate structures, wherein each of the ionized candidate structures have a same charge state; and determine, by relaxing each of the ionized candidate structures in a molecular dynamics simulation, the candidate molecule structure for each of the ionized candidate structures.

14. The device of claim 12, wherein determining the plurality of candidate molecular assemblies comprises:

docking, by a macromolecular docking algorithm, one or more of the molecule, one or more assemblies of the molecule, or a combination thereof, with one another to form the plurality of candidate molecular assemblies.

15. The device of claim 12, wherein determining the predicted TRIM-MS spectra for each of the candidate molecule structures or candidate molecular assemblies comprises:

determining collision cross sections for each of the candidate molecule structures or candidate molecular assemblies; and determining, based on the collision cross sections, the predicted TRIM-MS spectra for each of the candidate molecule structures or candidate molecular assemblies.

16. The device of claim 12, wherein the collision cross sections for each of the candidate molecule structures or candidate molecular assemblies is determined by projection superposition approximation (PSA) or local collision probability approximation (LCPA).

17. The device of claim 12, wherein the subset of candidate molecule structures or candidate molecular assemblies is each candidate molecule structure or each candidate molecular assembly whose corresponding predicted TRIM-MS spectra, when shifted by a $\delta\Omega$ value, overlaps with the measured TRIM-MS spectrum.

18. The device of claim 12, wherein [a] determining the candidate score for each candidate molecule structure in the subset comprises:

determining, for each candidate molecule structure in the subset, an atom-atom distance probability distribution for each atom-atom pair; and determining, for each candidate molecule structure in the subset, the candidate score based on a joint probability based on the atom-atom distance probability distribution for each atom-atom pair;

and [b] determining the candidate score for each candidate molecular assembly in the subset comprises:

cross-correlating the measured TRIM-MS spectrum of the molecular assembly of the molecule with each of the predicted TRIM-MS spectra; or determining a probability ranking for each candidate molecular assembly in the subset.

19. The device of claim 12, wherein assigning the molecular structure of the molecule or the molecular structure of the molecular assembly comprises:

determining the molecular structure of the molecule or the molecular assembly is the candidate molecule structure or the candidate molecular assembly corresponding to a highest ranking candidate score.

20. The device of claim 12, wherein the memory and processing circuitry are further configured to create a new data file or update an existing data file for the molecule, the data file comprising:

an identifier of the molecule; and the molecular structure of the molecule or the molecular structure of the molecular assembly.

21. The device of claim 12, wherein the memory and processing circuitry are further configured to provide the molecular structure of the molecule or the molecular structure of the molecular assembly by:

displaying an image of the molecular structure of the molecule or the molecular assembly, displaying coordinates of the molecular structure of the molecule or the molecular assembly, sending the image of the molecular structure of the molecule or the molecular assembly, sending coordinates of the molecular structure of the molecule or the molecular assembly, or a combination thereof.

22. A device for drug screening, the device comprising memory and processing circuitry configured to:

screen a potential therapeutic against the molecular structure of the molecule or against the molecular structure of the molecular assembly determined by the device according to claim 12.

* * * * *